US008808712B2

(12) United States Patent
Horii et al.

(10) Patent No.: US 8,808,712 B2
(45) Date of Patent: Aug. 19, 2014

(54) MALARIA VACCINE

(75) Inventors: Toshihiro Horii, Suita (JP); Ken Ishii, Suita (JP); Takahiro Tougan, Suita (JP)

(73) Assignee: Osaka University, Osaka (JP)

( * ) Notice: Subject to any disclaimer, the term of this patent is extended or adjusted under 35 U.S.C. 154(b) by 0 days.

(21) Appl. No.: 13/318,245

(22) PCT Filed: Apr. 30, 2010

(86) PCT No.: PCT/JP2010/057719
§ 371 (c)(1),
(2), (4) Date: Dec. 8, 2011

(87) PCT Pub. No.: WO2010/126151
PCT Pub. Date: Nov. 4, 2010

(65) Prior Publication Data
US 2012/0076816 A1    Mar. 29, 2012

(30) Foreign Application Priority Data
May 1, 2009 (JP) ................................. 2009-111967

(51) Int. Cl.
*A61K 39/015* (2006.01)
*A61K 39/00* (2006.01)
*A61K 38/00* (2006.01)
*C07K 1/00* (2006.01)

(52) U.S. Cl.
USPC .................. 424/268.1; 424/191.1; 424/192.1; 514/1.1; 530/350; 530/300; 530/820; 530/806

(58) Field of Classification Search
None
See application file for complete search history.

(56) References Cited

U.S. PATENT DOCUMENTS

| 2004/0137512 A1 | 7/2004 | Horii |
| 2007/0009994 A1 | 1/2007 | Horii |
| 2009/0041808 A1 | 2/2009 | Akira et al. |
| 2009/0104219 A1 | 4/2009 | Horii |

FOREIGN PATENT DOCUMENTS

| EP | 1 279 735 | 1/2003 |
| WO | 2002/059319 | 8/2002 |
| WO | 2006/061965 | 6/2006 |

OTHER PUBLICATIONS

The New Riverside University Dictionary. The Riverside Publishing Company, p. 933, 1984.*
Illustrated Stedman's Medical Dictionary, 24th Edition, Williams and Wilkins, London, p. 707, 1982.*

Extended European Search Report issued Jul. 11, 2012 in corresponding European Application No. 10769849.0.
Okech, Brenda, et al., "High Titers of IgG Antibodies Against *Plasmodium falciparum* Serine Repeat Antigen 5 (SERA5) Are Associated With Protection Against Severe Malaria in Ugandan Children", American Journal of Tropical Medicine and Hygiene, vol. 74, No. 2, 2006, pp. 191-197.
Fox, Barbara A., et al., "*Plasmodium falciparum*: fine-mapping of an epitope of the serine repeat antigen that is a target of parasite-inhibitory antibodies", Experimental Parasitology, vol. 101, No. 1, 2002, pp. 69-72.
Fox, Barbara A., et al., "*Plasmodium falciparum*: An Epitope within a Highly Conserved Region of the 47-kDa Amino-Terminal Domain of the Serine Repeat Antigen Is a Target of Parasite-Inhibitory Antibodies", Experimental Parasitology, vol. 85, No. 2, 1997, pp. 121-134.
Ishii, Ken J., et al., "Toll or Toll-Free Adjuvant Path Toward the Optimal Vaccine Development", Journal of Clinical Immunology, vol. 27, No. 4, 2007, pp. 363-371.
Verthelyi, Daniela, et al., "CpG Oligodeoxynucleotides as Vaccine Adjuvants in Primates", Journal of Immunology, vol. 168, No. 4, 2002, pp. 1659-1663.
Sugiyama, Takahiro, et al., "CpG RNA: Identification of Novel Single-Stranded RNA That Stimulates Human $CD14^+$ $CD11c^+$ Monocytes", The Journal of Immunology, vol. 174, No. 4, 2005, pp. 2273-2279.
International Search Report issued Aug. 10, 2010 in corresponding International Application No. PCT/JP2010/057719, of record.
Toshihiro Horii, "Malaria Vaccine", Japanese Journal of Clinical Medicine, vol. 66, No. 10, Oct. 2008, pp. 1990-1998 with English Abstract.
David J. Bzik, et al., "Amino acid sequence of the serine-repeat antigen (SERA) of *Plasmodium falciparum* determined from cloned cDNA", Molecular and Biochemical Parasitology, vol. 30, 1998, pp. 279-288.

\* cited by examiner

*Primary Examiner* — S. Devi
(74) *Attorney, Agent, or Firm* — Wenderoth, Lind & Ponack, L.L.P.

(57) ABSTRACT

The present invention provides a vaccine for preventing and/or treating *Plasmodium falciparum* infections, which comprises a polypeptide set forth in SEQ ID NO: 1 or represented by formula (1), and an adjuvant.

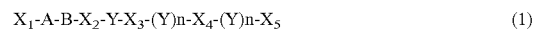

$$X_1\text{-}A\text{-}B\text{-}X_2\text{-}Y\text{-}X_3\text{-}(Y)n\text{-}X_4\text{-}(Y)n\text{-}X_5 \qquad (1)$$

(In the formula, $X_1$ represents the 1st to 7th amino acid residues in a polypeptide set forth in SEQ ID NO: 1; $X_2$ represents the 73th to 177th amino acid residues; $X_3$ represents the 178th to 258th amino acid residues; $X_4$ represents the 259th to 289th amino acid residues; $X_5$ represents the 290th to 334th amino acid residues; A represents an 8-mer repeat sequence contained in a 47-kd region of SERA polypeptide of *Plasmodium falciparum*; B represents a sequence of a serine-rich region contained in a 47-kd region of SERA polypeptide of *Plasmodium falciparum*; Y represents any one selected from A-A, A-B, and B; and n is an integer of 0 or 1.)

5 Claims, 13 Drawing Sheets

Fig. 1-1

<Amino Acid Sequence>
Original SE36 (SEQ ID NO: 1)
MKNVIKCTGESQTGNTGGGQAGNTVGDQAGSTGGSPQGSTGASQPGSSEPSNPVSSG
HSVSTVSVSQTSTSSEKQDTIQVKSALLKDYMGLKVTGPCNENFIMFLVPHIYIDVDTE
DTNIELRTTLKETNNAISFESNSGSLEKKKYVKLPSNGTTGEQGSSTGTVRGDTEPISDS
SESLPANGPDSPTVKPPRNLQNICETGKNFKLVVYIKENTLIIKWKVYGETKDTTENNK
VDVRKYLINEKETPFTSILIHAYKEHNGTNLIESKNYALGSDIPEKCDTLASNCFLSGNF
NIEKCFQCALLVEKENKNDVCYKYLSEDIVSNFKEIKAE SE36-1 (SEQ ID NO: 10)
MKNVIKCTGESQTGNTGGGQAGNTVGDQAGSTGGSPQGSTGASQPGSSEPSNPVSSG
HSVSTVSVSQTSTSSEKQDTIQVKSALLKDYMGLKVTGPCNENFIMFLVPHIYIDVDTE
DTNIELRTTLKETNNAISFESNSGSLEKKKYVKLPSNGTTGEQGSSTGTVRGDTEPISDS
STGESQTGNTGGGQAGNTGGDQAGSTGGSPQGSTGASPQGSTGASPQGSTGASQPGSS
EPSNPVSSGHSVSTVSVSQTSTSSDSSESLPANGPDSPTVKPPRNLQNICETGKNFKLVV
YIKENTLIIKWKVYGETKDTTENNKVDVRKYLINEKETPFTSILIHAYKEHNGTNLIESK
NYALGSDIPEKCDTLASNCFLSGNFNIEKCFQCALLVEKENKNDVCYKYLSEDIVSNFK
EIKAE SE36-2 (SEQ ID NO: 11)
MKNVIKCTGESQTGNTGGGQAGNTVGDQAGSTGGSPQGSTGASQPGSSEPSNPVSSG
HSVSTVSVSQTSTSSEKQDTIQVKSALLKDYMGLKVTGPCNENFIMFLVPHIYIDVDTE
DTNIELRTTLKETNNAISFESNSGSLEKKKYVKLPSNGTTGEQGSSTGTVRGDTEPISDS
STGESQTGNTGGGQAGNTGGDQAGSTGGSPQGSTGASPQGSTGASPQGSTGASQPGSS
EPSNPVSSGHSVSTVSVSQTSTSSDSSESLPANGPDSPTVKPPRNLQNICETGKNFKLVV
YIKENTLIIKWKVYGETKDTTENNKVDVRKYLINEKETPFTSILIHAYTGESQTGNTGG
GQAGNTVGDQAGNTVGDQAGSTGGSPQGSTGASQPGSSEPSNPVSSGHSVSTVSVSQT
STSSHAYKEHNGTNLIESKNYALGSDIPEKCDTLASNCFLSGNFNIEKCFQCALLVEKE
NKNDVCYKYLSEDIVSNFKEIKAE SE36-3 (SEQ ID NO: 12)
MKNVIKCTGESQTGNTGGGQAGNTVGDQAGSTGGSPQGSTGASQPGSSEPSNPVSSG
HSVSTVSVSQTSTSSEKQDTIQVKSALLKDYMGLKVTGPCNENFIMFLVPHIYIDVDTE
DTNIELRTTLKETNNAISFESNSGSLEKKKYVKLPSNGTTGEQGSSTGTVRGDTEPISDS
STGESQTGNTGGGQAGNTGGDQAGSTGGSPQGSTGASPQGSTGASPQGSTGASQPGSS
EPSNPVSSGHSVSTVSVSQTSTSSDSSESLPANGPDSPTVKPPRNLQNICETGKNFKLVV
YIKENTLIIKWKVYGETKDTTENNKVDVRKYLINEKETPFTSILIHAYTGESQTGNTGG
GQAGNTVGDQAGNTVGDQAGSTGGSPQGSTGASQPGSSEPSNPVSSGHSVSTVSVSQT
STSSHAYKEHNGTNLIESKNYALGSDIPEKCDTLASNCTGESQTGNTGGGQAGNTGGG
QAGNTVGDQAGSTGGSPQGSTGASQPGSSEPSNPVSSGHSVSTVSVSQTSTSSSNCFLS
GNFNIEKCFQCALLVEKENKNDVCYKYLSEDIVSNFKEIKAE

Fig. 1-2

SE36-4 (SEQ ID NO: 13)
MKNVIKCTGESQTGNTGGGQAGNTVGDQAGSTGGSPQGSTGASQPGSSEPSNPVSSG
HSVSTVSVSQTSTSSEKQDTIQVKSALLKDYMGLKVTGPCNENFIMFLVPHIYIDVDTE
DTNIELRTTLKETNNAISFESNSGSLEKKKYVKLPSNGTTGEQGSSTGTVRGDTEPISDS
STGESQTGNTGGGQAGNTGGDQAGSTGGSPQGSTGASPQGSTGASPQGSTGASQPGSG
STGESQTGNTGGGQVGNTGGGQAGSTGGSPQGSTGASQPGSSEPSNPVSDSSESLPAN
GPDSPTVKPPRNLQNICETGKNFKLVVYIKENTLIIKWKVYGETKDTTENNKVDVRKYL
INEKETPFTSILIHAYTGESQTGNTGGGQAGNTVGDQAGNTVGDQAGSTGGSPQGSTG
ASQPGSLKTGESQTGNTGGGQAGNTVGGQAGNTGGGQAGNTGGDPQGSTGGSQPGS
HAYKEHNGTNLIESKNYALGSDIPEKCDTLASNCTGESQTGNTGGGQAGNTGGGQAG
NTVGDQAGSTGGSPQGSTGASQPGSLETGESQTGNAGGGQAGNTVGDQAGSTGGSPQ
GSTGASPQGSTGASPQGSTGASQPGSSNCFLSGNFNIEKCFQCALLVEKENKNDVCYK
YLSEDIVSNFKEIKAE

SE36-5 (SEQ ID NO: 14)
MKNVIKCTGESQTGNTGGGQAGNTVGDQAGSTGGSPQGSTGASQPGSSEPSNPVSSG
HSVSTVSVSQTSTSSEKQDTIQVKSALLKDYMGLKVTGPCNENFIMFLVPHIYIDVDTE
DTNIELRTTLKETNNAISFESNSGSLEKKKYVKLPSNGTTGEQGSSTGTVRGDTEPISDS
SSEPSNPVSSGHSVSTVSVSQTSTSSDSSESLPANGPDSPTVKPPRNLQNICETGKNFKL
VVYIKENTLIIKWKVYGETKDTTENNKVDVRKYLINEKETPFTSILIHAYSEPSNPVSSG
HSVSTVSVSQTSTSSHAYKEHNGTNLIESKNYALGSDIPEKCDTLASNCSEPSNPVSSGH
SVSTVSVSQTSTSSSNCFLSGNFNIEKCFQCALLVEKENKNDVCYKYLSEDIVSNFKEIK
AE

Negative SE36 (SEQ ID NO: 15)
MSEKQDTIQVKSALLKDYMGLKVTGPCNENFIMFLVPHIYIDVDTEDTNIELRTTLKET
NNAISFESNSGSLEKKKYVKLPSNGTTGEQGSSTGTVRGDTEPISDSSESLPANGPDSPT
VKPPRNLQNICETGKNFKLVVYIKENTLIIKWKVYGETKDTTENNKVDVRKYLINEKET
PFTSILIHAYKEHNGTNLIESKNYALGSDIPEKCDTLASNCFLSGNFNIEKCFQCALLVE
KENKNDVCYKYLSEDIVSNFKEIKAE

Fig. 1-3

<Nucleotide Sequence>
Original SE36 (SEQ ID NO: 16)
ATGAAAAACGTGATCAAATGTACCGGTGAAAGCCAGACCGGTAATACCGGCGGTGGTC
AGGCAGGCAACACGGTTGGCGACCAGGCGGGCTCTACCGGCGGCTCTCCGCAGGGTA
GCACAGGCGCCAGTCAACCCGGCTCTAGCGAACCGTCTAACCCAGTGTCTTCTGGCCA
TTCTGTTAGTACCGTTAGCGTTAGCCAGACCAGCACCTCTTCTGAAAAACAAGATACCA
TTCAGGTGAAATCTGCGCTGCTGAAAGATTATATGGGTTTAAAAGTTACGGGCCCGTG
TAACGAAAATTTCATCATGTTCCTGGTTCCGCATATTTATATTGATGTGGATACCGAAGA
TACCAATATAGAGCTCCGTACCACCCTGAAAGAAACCAACAACGCGATCTCATTTGAAT
CAAACAGTGGTTCACTGGAAAAAAAAAAATATGTGAAGCTTCCGTCAAACGGCACCAC
CGGTGAACAGGGTTCAAGTACAGGCACCGTTCGCGGCGATACCGAACCGATTTCAGA
CTCGAGTGAAAGTCTTCCGGCGAATGGCCCGGATTCCCCGACCGTTAAACCCCCGCGT
AACCTGCAGAACATCTGTGAAACCGGCAAAAACTTCAAACTGGTGGTGTATATTAAGG
AGAATACATTAATCATTAAATGGAAAGTGTACGGCGAAACCAAAGATACCACCGAAAAT
AACAAAGTGGACGTACGCAAGTATCTGATTAACGAAAAGGAAACCCCGTTTACTAGTA
TTCTAATCCATGCATATAAAGAACATAATGGCACCAACCTGATCGAAAGTAAAAACTAC
GCGCTGGGCTCAGACATTCCGGAAAAATGTGATACCCTGGCGTCCAATTGCTTTCTGA
GTGGTAACTTTAACATTGAAAAATGCTTTCAGTGCGCGCTGCTGGTGGAAAAAGAAAA
TAAAAACGACGTGTGTTACAAATACCTAAGCGAAGATATTGTGTCTAATTTCAAGGAGA
TCAAAGCGGAGTAA

Fig. 1-4

SE36-1 (SEQ ID NO: 16)
ATGAAAAACGTGATCAAATGTACCGGTGAAAGCCAGACCGGTAATACCGGCGGTGGTC
AGGCAGGCAACACGGTTGGCGACCAGGCGGGCTCTACCGGCGGCTCTCCGCAGGGTA
GCACAGGCGCCAGTCAACCCGGCTCTAGCGAACCGTCTAACCCAGTGTCTTCTGGCCA
TTCTGTTAGTACCGTTAGCGTTAGCCAGACCAGCACCTCTTCTGAAAAACAAGATACCA
TTCAGGTGAAATCTGCGCTGCTGAAAGATTATATGGGTTTAAAAGTTACGGGCCCGTG
TAACGAAAATTTCATCATGTTCCTGGTTCCGCATATTTATATTGATGTGGATACCGAAGA
TACCAATATAGAGCTCCGTACCACCCTGAAAGAAACCAACAACGCGATCTCATTTGAAT
CAAACAGTGGTTCACTGGAAAAAAAAAAATATGTGAAGCTTCCGTCAAACGGCACCAC
CGGTGAACAGGGTTCAAGTACAGGCACCGTTCGCGGCGATACCGAACCGATTTCAGA
CTCGAGTACCGGTGAATCTCAAACCGGTAACACTGGTGGCGGTCAGGCAGGTAACAC
CGGCGGAGATCAGGCAGGAAGCACCGGCGGCAGCCCGCAAGGAAGCACAGGCGCGA
GTCCGCAGGGTAGCACTGGTGCGAGCCCACAGGGTAGTACAGGCGCAAGTCAACCTG
GAAGCTCTGAACCGAGTAACCCGGTTAGCTCTGGACATAGTGTTAGTACCGTTTCGGT
TTCTCAGACGTCTACGAGTTCGGACTCGAGTGAAAGTCTTCCGGCGAATGGCCCGGAT
TCCCCGACCGTTAAACCCCCGCGTAACCTGCAGAACATCTGTGAAACCGGCAAAAACT
TCAAACTGGTGGTGTATATTAAGGAGAATACATTAATCATTAAATGGAAAGTGTACGGC
GAAACCAAAGATACCACCGAAAATAACAAAGTGGACGTACGCAAGTATCTGATTAACG
AAAAGGAAACCCCGTTTACTAGTATTCTAATCCATGCATATAAAGAACATAATGGCACC
AACCTGATCGAAAGTAAAAACTACGCGCTGGGCTCAGACATTCCGGAAAAATGTGATA
CCCTGGCGTCCAATTGCTTTCTGAGTGGTAACTTTAACATTGAAAAATGCTTTCAGTGC
GCGCTGCTGGTGGAAAAAGAAAATAAAAACGACGTGTGTTACAAATACCTAAGCGAAG
ATATTGTGTCTAATTTCAAGGAGATCAAAGCGGAGTAA

Fig. 1-5

SE36-2 (SEQ ID NO: 18)
ATGAAAAACGTGATCAAATGTACCGGTGAAAGCCAGACCGGTAATACCGGCGGTGGTC
AGGCAGGCAACACGGTTGGCGACCAGGCGGGCTCTACCGGCGGCTCTCCGCAGGGTA
GCACAGGCGCCAGTCAACCCGGCTCTAGCGAACCGTCTAACCCAGTGTCTTCTGGCCA
TTCTGTTAGTACCGTTAGCGTTAGCCAGACCAGCACCTCTTCTGAAAAACAAGATACCA
TTCAGGTGAAATCTGCGCTGCTGAAAGATTATATGGGTTTAAAAGTTACGGGCCCGTG
TAACGAAAATTTCATCATGTTCCTGGTTCCGCATATTTATATTGATGTGGATACCGAAGA
TACCAATATAGAGCTCCGTACCACCCTGAAAGAAACCAACAACGCGATCTCATTTGAAT
CAAACAGTGGTTCACTGGAAAAAAAAAAATATGTGAAGCTTCCGTCAAACGGCACCAC
CGGTGAACAGGGTTCAAGTACAGGCACCGTTCGCGGCGATACCGAACCGATTTCAGA
CTCGAGTACCGGTGAATCTCAAACCGGTAACACTGGTGGCGGTCAGGCAGGTAACAC
CGGCGGAGATCAGGCAGGAAGCACCGGCGGCAGCCCGCAAGGAAGCACAGGCGCGA
GTCCGCAGGGTAGCACTGGTGCGAGCCCACAGGGTAGTACAGGCGCAAGTCAACCTG
GAAGCTCTGAACCGAGTAACCCGGTTAGCTCTGGACATAGTGTTAGTACCGTTTCGGT
TTCTCAGACGTCTACGAGTTCGGACTCGAGTGAAAGTCTTCCGGCGAATGGCCCGGAT
TCCCCGACCGTTAAACCCCGCGTAACCTGCAGAACATCTGTGAAACCGGCAAAAACT
TCAAACTGGTGGTGTATATTAAGGAGAATACATTAATCATTAAATGGAAAGTGTACGGC
GAAACCAAAGATACCACCGAAAATAACAAAGTGGACGTACGCAAGTATCTGATTAACG
AAAAGGAAACCCCGTTTACTAGTATTCTAATCCATGCATATACCGGCGAAAGCCAAACG
GGCAACACAGGTGGTGGTCAGGCCGGTAATACTGTGGGCGATCAAGCTGGTAACACC
GTGGGCGATCAGGCGGGCTCTACAGGTGGCAGCCCTCAGGGCAGCACCGGAGCATCT
CAACCTGGTAGTAGCGAGCCGTCTAATCCAGTGAGCTCTGGTCATTCCGTTAGCACCG
TGAGCGTGAGTCAGACGAGCACGAGCTCGCATGCATATAAAGAACATAATGGCACCAA
CCTGATCGAAAGTAAAAACTACGCGCTGGGCTCAGACATTCCGGAAAAATGTGATACC
CTGGCGTCCAATTGCTTTCTGAGTGGTAACTTTAACATTGAAAAATGCTTTCAGTGCGC
GCTGCTGGTGGAAAAAGAAAATAAAAACGACGTGTGTTACAAATACCTAAGCGAAGAT
ATTGTGTCTAATTTCAAGGAGATCAAAGCGGAGTAA

Fig. 1-6

SE36-3 (SEQ ID NO: 19)
ATGAAAAACGTGATCAAATGTACCGGTGAAAGCCAGACCGGTAATACCGGCGGTGGTC
AGGCAGGCAACACGGTTGGCGACCAGGCGGGCTCTACCGGCGGCTCTCCGCAGGGTA
GCACAGGCGCCAGTCAACCCGGCTCTAGCGAACCGTCTAACCCAGTGTCTTCTGGCCA
TTCTGTTAGTACCGTTAGCGTTAGCCAGACCAGCACCTCTTCTGAAAAACAAGATACCA
TTCAGGTGAAATCTGCGCTGCTGAAAGATTATATGGGTTTAAAAGTTACGGGCCCGTG
TAACGAAAATTTCATCATGTTCCTGGTTCCGCATATTTATATTGATGTGGATACCGAAGA
TACCAATATAGAGCTCCGTACCACCCTGAAAGAAACCAACAACGCGATCTCATTTGAAT
CAAACAGTGGTTCACTGGAAAAAAAAAAATATGTGAAGCTTCCGTCAAACGGCACCAC
CGGTGAACAGGGTTCAAGTACAGGCACCGTTCGCGGCGATACCGAACCGATTTCAGA
CTCGAGTACCGGTGAATCTCAAACCGGTAACACTGGTGGCGGTCAGGCAGGTAACAC
CGGCGGAGATCAGGCAGGAAGCACCGGCGGCAGCCCGCAAGGAAGCACAGGCGCGA
GTCCGCAGGGTAGCACTGGTGCGAGCCCACAGGGTAGTACAGGCGCAAGTCAACCTG
GAAGCTCTGAACCGAGTAACCCGGTTAGCTCTGGACATAGTGTTAGTACCGTTTCGGT
TTCTCAGACGTCTACGAGTTCGGACTCGAGTGAAAGTCTTCCGGCGAATGGCCCGGAT
TCCCCGACCGTTAAACCCCCGCGTAACCTGCAGAACATCTGTGAAACCGGCAAAAACT
TCAAACTGGTGGTGTATATTAAGGAGAATACATTAATCATTAAATGGAAAGTGTACGGC
GAAACCAAAGATACCACCGAAAATAACAAAGTGGACGTACGCAAGTATCTGATTAACG
AAAAGGAAACCCCGTTTACTAGTATTCTAATCCATGCATATACCGGCGAAAGCCAAACG
GGCAACACAGGTGGTGGTCAGGCCGGTAATACTGTGGGCGATCAAGCTGGTAACACC
GTGGGCGATCAGGCGGGCTCTACAGGTGGCAGCCCTCAGGGCAGCACCGGAGCATCT
CAACCTGGTAGTAGCGAGCCGTCTAATCCAGTGAGCTCTGGTCATTCCGTTAGCACCG
TGAGCGTGAGTCAGACGAGCACGAGCTCGCATGCATATAAAGAACATAATGGCACCAA
CCTGATCGAAAGTAAAAACTACGCGCTGGGCTCAGACATTCCGGAAAAATGTGATACC
CTGGCGTCCAATTGCACCGGCGAGAGCCAAACTGGCAACACGGGTGGTGGACAGGCT
GGTAACACTGGTGGCGGTCAGGCAGGCAATACTGTTGGTGATCAAGCTGGTAGTACC
GGCGGCAGTCCACAAGGAAGTACTGGAGCGAGCCAACCGGGCTCTAGCGAACCGAGC
AACCCGGTGAGCAGTGGACATAGCGTGAGCACCGTTAGCGTTAGTCAGACCTCGACC
AGCAGTTCCAATTGCTTTCTGAGTGGTAACTTTAACATTGAAAAATGCTTTCAGTGCGC
GCTGCTGGTGGAAAAAGAAAATAAAAACGACGTGTGTTACAAATACCTAAGCGAAGAT
ATTGTGTCTAATTTCAAGGAGATCAAAGCGGAGTAA

Fig. 1-7

SE36-4 (SEQ ID NO: 20)
ATGAAAAACGTGATCAAATGTACCGGTGAAAGCCAGACCGGTAATACCGGCGGTGGTC
AGGCAGGCAACACGGTTGGCGACCAGGCGGGCTCTACCGGCGGCTCTCCGCAGGGTA
GCACAGGCGCCAGTCAACCCGGCTCTAGCGAACCGTCTAACCCAGTGTCTTCTGGCCA
TTCTGTTAGTACCGTTAGCGTTAGCCAGACCAGCACCTCTTCTGAAAAACAAGATACCA
TTCAGGTGAAATCTGCGCTGCTGAAAGATTATATGGGTTTAAAAGTTACGGGCCCGTG
TAACGAAAATTTCATCATGTTCCTGGTTCCGCATATTTATATTGATGTGGATACCGAAGA
TACCAATATAGAGCTCCGTACCACCCTGAAAGAAACCAACAACGCGATCTCATTTGAAT
CAAACAGTGGTTCACTGGAAAAAAAAAAATATGTGAAGCTTCCGTCAAACGGCACCAC
CGGTGAACAGGGTTCAAGTACAGGCACCGTTCGCGGCGATACCGAACCGATTTCAGA
CTCGAGTACCGGTGAATCTCAAACCGGTAACACTGGTGGCGGTCAGGCAGGTAACAC
CGGCGGAGATCAGGCAGGAAGCACCGGCGGCAGCCCGCAAGGAAGCACAGGCGCGA
GTCCGCAGGGTAGCACTGGTGCGAGCCCACAGGGTAGTACAGGCGCAAGTCAACCTG
GAAGCGGATCCACGGGTGAGTCGCAAACTGGTAATACGGGTGGAGGCCAAGTGGGCA
ATACTGGTGGTGGCCAGGCAGGTTCGACTGGAGGTTCTCCGCAAGGCTCTACCGGTG
CAAGCCAACCAGGAAGCAGTGAACCGTCTAATCCGGTGAGCGACTCGAGTGAAAGTC
TTCCGGCGAATGGCCCGGATTCCCCGACCGTTAAACCCCCGCGTAACCTGCAGAACAT
CTGTGAAACCGGCAAAAACTTCAAACTGGTGGTGTATATTAAGGAGAATACATTAATCA
TTAAATGGAAAGTGTACGGCGAAACCAAAGATACCACCGAAAATAACAAAGTGGACGT
ACGCAAGTATCTGATTAACGAAAGGAAACCCCGTTTACTAGTATTCTAATCCATGCAT
ATACCGGCGAAAGCCAAACGGGCAACACAGGTGGTGGTCAGGCCGGTAATACTGTGG
GCGATCAAGCTGGTAACACCGTGGGCGATCAGGCGGGCTCTACAGGTGGCAGCCCTC
AGGGCAGCACCGGAGCATCTCAACCTGGTAGTCTTAAGACGGGTGAATCACAGACCG
GTAATACCGGAGGCGGACAAGCAGGTAATACCGTTGGAGGCCAGGCTGGTAATACGG
GAGGTGGTCAGGCAGGTAATACTGGCGGAGATCCGCAAGGTAGTACCGGTGGAAGCC
AACCAGGCTCCCATGCATATAAAGAACATAATGGCACCAACCTGATCGAAAGTAAAAA
CTACGCGCTGGGCTCAGACATTCCGGAAAAATGTGATACCCTGGCGTCCAATTGCACC
GGCGAGAGCCAAACTGGCAACACGGGTGGTGGACAGGCTGGTAACACTGGTGGCGG
TCAGGCAGGCAATACTGTTGGTGATCAAGCTGGTAGTACCGGCGGCAGTCCACAAGG
AAGTACTGGAGCGAGCCAACCGGGCTCTCTCGAGACGGGCGAAAGTCAGACGGGTAA
CGCAGGTGGAGGTCAAGCAGGCAACACGGTTGGTGACCAAGCAGGTAGCACGGGTG
GAAGTCCGCAAGGTAGTACAGGTGCAAGTCCACAAGGCTCCACTGGTGCATCTCCAC
AAGGTTCGACCGGTGCAAGTCAGCCGGGTAGCTCCAATTGCTTTCTGAGTGGTAACTT
TAACATTGAAAATGCTTTCAGTGCGCGCTGCTGGTGGAAAAAGAAAATAAAAACGAC
GTGTGTTACAAATACCTAAGCGAAGATATTGTGTCTAATTTCAAGGAGATCAAAGCGGA
GTAA

Fig. 1-8

SE36-5 (SEQ ID NO: 21)
ATGAAAAACGTGATCAAATGTACCGGTGAAAGCCAGACCGGTAATACCGGCGGTGGTC
AGGCAGGCAACACGGTTGGCGACCAGGCGGGCTCTACCGGCGGCTCTCCGCAGGGTA
GCACAGGCGCCAGTCAACCCGGCTCTAGCGAACCGTCTAACCCAGTGTCTTCTGGCCA
TTCTGTTAGTACCGTTAGCGTTAGCCAGACCAGCACCTCTTCTGAAAAACAAGATACCA
TTCAGGTGAAATCTGCGCTGCTGAAAGATTATATGGGTTTAAAAGTTACGGGCCCGTG
TAACGAAAATTTCATCATGTTCCTGGTTCCGCATATTTATATTGATGTGGATACCGAAGA
TACCAATATAGAGCTCCGTACCACCCTGAAAGAAACCAACAACGCGATCTCATTTGAAT
CAAACAGTGGTTCACTGGAAAAAAAAAAATATGTGAAGCTTCCGTCAAACGGCACCAC
CGGTGAACAGGGTTCAAGTACAGGCACCGTTCGCGGCGATACCGAACCGATTTCAGA
CTCGAGTTCTGAACCGAGTAACCCGGTTAGCTCTGGACATAGTGTTAGTACCGTTTCG
GTTTCTCAGACGTCTACGAGTTCGGACTCGAGTGAAAGTCTTCCGGCGAATGGCCCG
GATTCCCCGACCGTTAAACCCCCGCGTAACCTGCAGAACATCTGTGAAACCGGCAAAA
ACTTCAAACTGGTGGTGTATATTAAGGAGAATACATTAATCATTAAATGGAAAGTGTAC
GGCGAAACCAAAGATACCACCGAAAATAACAAAGTGGACGTACGCAAGTATCTGATTA
ACGAAAAGGAAACCCCGTTTACTAGTATTCTAATCCATGCATATAGCGAGCCGTCTAAT
CCAGTGAGCTCTGGTCATTCCGTTAGCACCGTGAGCGTGAGTCAGACGAGCACGAGC
TCGCATGCATATAAAGAACATAATGGCACCAACCTGATCGAAAGTAAAAACTACGCGCT
GGGCTCAGACATTCCGGAAAAATGTGATACCCTGGCGTCCAATTGCAGCGAACCGAGC
AACCCGGTGAGCAGTGGACATAGCGTGAGCACCGTTAGCGTTAGTCAGACCTCGACC
AGCAGTTCCAATTGCTTTCTGAGTGGTAACTTTAACATTGAAAAATGCTTTCAGTGCGC
GCTGCTGGTGGAAAAAGAAAATAAAAACGACGTGTGTTACAAATACCTAAGCGAAGAT
ATTGTGTCTAATTTCAAGGAGATCAAAGCGGAGTAA

Negative SE36 (SEQ ID NO: 22)
ATGTCTGAAAAACAAGATACCATTCAGGTGAAATCTGCGCTGCTGAAAGATTATATGG
GTTTAAAAGTTACGGGCCCGTGTAACGAAAATTTCATCATGTTCCTGGTTCCGCATATT
TATATTGATGTGGATACCGAAGATACCAATATAGAGCTCCGTACCACCCTGAAAGAAAC
CAACAACGCGATCTCATTTGAATCAAACAGTGGTTCACTGGAAAAAAAAAAATATGTG
AAGCTTCCGTCAAACGGCACCACCGGTGAACAGGGTTCAAGTACAGGCACCGTTCGC
GGCGATACCGAACCGATTTCAGACTCGAGTGAAAGTCTTCCGGCGAATGGCCCGGATT
CCCCGACCGTTAAACCCCCGCGTAACCTGCAGAACATCTGTGAAACCGGCAAAAACTT
CAAACTGGTGGTGTATATTAAGGAGAATACATTAATCATTAAATGGAAAGTGTACGGCG
AAACCAAAGATACCACCGAAAATAACAAAGTGGACGTACGCAAGTATCTGATTAACGA
AAAGGAAACCCCGTTTACTAGTATTCTAATCCATGCATATAAAGAACATAATGGCACCA
ACCTGATCGAAAGTAAAAACTACGCGCTGGGCTCAGACATTCCGGAAAAATGTGATAC
CCTGGCGTCCAATTGCTTTCTGAGTGGTAACTTTAACATTGAAAAATGCTTTCAGTGCG
CGCTGCTGGTGGAAAAAGAAAATAAAAACGACGTGTGTTACAAATACCTAAGCGAAGA
TATTGTGTCTAATTTCAAGGAGATCAAAGCGGAGTAA

Fig. 1-9

<Polypeptides for Epitope Mapping>

SERA36-42aa-peptide-1
MKNVIKCTGESQTGNTGGGQAGNTVGDQAGSTGGSPQGSTGA (SEQ ID NO: 23)

SERA36-42aa-peptide-2
NTVGDQAGSTGGSPQGSTGASQPGSSEPSNPVSSGHSVSTVS (SEQ ID NO: 24)

SERA36-42aa-peptide-3
SQPGSSEPSNPVSSGHSVSTVSVSQTSTSSEKQDTIQVKSAL (SEQ ID NO: 25)

SERA36-42aa-peptide-4
VSQTSTSSEKQDTIQVKSALLKDYMGLKVTGPCNENFIMFLV (SEQ ID NO: 26)

SERA36-42aa-peptide-5
LKDYMGLKVTGPCNENFIMFLVPHIYIDVDTEDTNIELRTTL (SEQ ID NO: 27)

SERA36-42aa-peptide-6
PHIYIDVDTEDTNIELRTTLKETNNAISFESNSGSLEKKKYV (SEQ ID NO: 28)

SERA36-42aa-peptide-7
KETNNAISFESNSGSLEKKKYVKLPSNGTTGEQGSSTGTVRG (SEQ ID NO: 29)

SERA36-42aa-peptide-8
KLPSNGTTGEQGSSTGTVRGDTEPISDSSESLPANGPDSPTV (SEQ ID NO: 30)

SERA36-42aa-peptide-9
DTEPISDSSESLPANGPDSPTVKPPRNLQNICETGKNFKLVV (SEQ ID NO: 31)

SERA36-42aa-peptide-10
KPPRNLQNICETGKNFKLVVYIKENTLIIKWKVYGETKDTTE (SEQ ID NO: 32)

SERA36-42aa-peptide-11
YIKENTLIIKWKVYGETKDTTENNKVDVRKYLINEKETPFTS (SEQ ID NO: 33)

SERA36-42aa-peptide-12
NNKVDVRKYLINEKETPFTSILIHAYKEHNGTNLIESKNYAL (SEQ ID NO: 34)

SERA36-42aa-peptide-13
ILIHAYKEHNGTNLIESKNYALGSDIPEKCDTLASNCFLSGN (SEQ ID NO: 35)

SERA36-42aa-peptide-14
GSDIPEKCDTLASNCFLSGNFNIEKCFQCALLVEKENKNDVC (SEQ ID NO: 36)

SERA36-40aa-peptide-15
FNIEKCFQCALLVEKENKNDVCYKYLSEDIVSNFKEIKAE (SEQ ID NO: 37)

MALARIA VACCINE

TECHNICAL FIELD

The present invention relates to a high-immunogenicity polypeptide that is useful as a malaria vaccine. The present invention relates to a vaccine that is useful for preventing and treating malaria parasite infections, and a diagnostic agent for malaria parasite infections.

BACKGROUND ART

Infectious diseases annually cause huge human and social damage in developing countries and elsewhere. In particular, malaria parasite infections annually infect 500 million people and cause the death of 2 million to 3 million people; however, no effective vaccine for the prevention of this disease has been developed. Therefore, there is an urgent need to develop a malaria vaccine.

However, in spite of many vaccine clinical tests conducted over the past 30 to 40 years, none of the developed vaccines showed efficacy and all efforts for vaccine development have been frustrated. In such circumstances, as a molecule recognized by an antibody having antimalarial activity, SERA (serine repeat antigen) protein was identified in the serum of adults who have acquired protective immunity (see, for example, Non-patent Literature (NPL) 1).

Later, the development of vaccines was conducted using recombinant SERA protein as an antigen. However, because the antibody titer of the obtained anti-SERA protein antibody is lower than that of Africans who have gained protection (immunity) against malaria parasite infections, further improvement has been desired.

CITATION LIST

Non-Patent Literature

NPL 1: Bzik D J, Li W B, Horii T, Inselburg J. Mol Biochem Parasitol. 1988 September; 30(3): 279-88

SUMMARY OF INVENTION

Technical Problem

A primary object of the present invention is to provide a high-immunogenicity polypeptide that is useful as a malaria vaccine, and to provide the use of the polypeptide as a vaccine against malaria parasite infections. Another object of the present invention is to provide an antibody to the polypeptide, and the use of the antibody or the polypeptide as a diagnostic agent for malaria parasite infections.

Solution to Problem

The present inventors previously identified that an 8-mer repeat region and/or a serine-rich region, which are present on the N-terminus of a SERA (serine repeat antigen) polypeptide, are protective epitopes of antibodies to *Plasmodium falciparum*.

Now the present inventors have found a polypeptide that has excellent immunogenicity and is useful as a malaria vaccine. In addition, the present inventors have found an optimal adjuvant for enhancing the immunogenicity of a malaria vaccine. The inventors conducted further research based on these findings and accomplished the present invention.

The present invention includes the following embodiments.

(I) Polypeptide Useful as a Malaria Vaccine, and Polynucleotide Encoding the Polypeptide (I-1) A polypeptide represented by the following formula (1):

$$X_1\text{-}A\text{-}B\text{-}X_2\text{-}Y\text{-}X_3\text{-}(Y)n\text{-}X_4\text{-}(Y)n\text{-}X_5 \tag{1}$$

(wherein
$X_1$ represents the 1st to 7th amino acid residues in a polypeptide set forth in SEQ ID NO: 1;
$X_2$ represents the 73th to 177th amino acid residues of the polypeptide;
$X_3$ represents the 178th to 258th amino acid residues of the polypeptide;
$X_4$ represents the 259th to 289th amino acid residues of the polypeptide;
$X_5$ represents the 290th to 334th amino acid residues of the polypeptide;
A represents an 8-mer repeat sequence contained in a 47-kd region of SERA polypeptide of *Plasmodium falciparum*;
B represents a sequence of a serine-rich region contained in a 47-kd region of SERA polypeptide of *Plasmodium falciparum*;
Y represents any one selected from A-A, A-B, and B; and
n represents an integer of 0 or 1).

(I-2) The polypeptide according to (I-1), wherein, in formula (1), Y is A-B or B.

(I-3) The polypeptide according to (I-1), wherein, in formula (1), A is an amino acid sequence selected from SEQ ID NOS: 2 to 8, and B is an amino acid sequence set forth in SEQ ID NO: 9.

(I-4) The polypeptide according to (I-1), wherein the polypeptide represented by formula (1) is a polypeptide represented by one of the formulas (2) to (6):

$$X_1\text{-}A_1\text{-}B\text{-}X_2\text{-}(A_2\text{-}B)\text{-}X_3\text{-}X_4\text{-}X_5 \tag{2}$$

$$X_1\text{-}A_1\text{-}B\text{-}X_2\text{-}(A_2\text{-}B)\text{-}X_3\text{-}(A_3\text{-}B)\text{-}X_4\text{-}X_5 \tag{3}$$

$$X_1\text{-}k\text{-}B\text{-}X_2\text{-}(A_2\text{-}B)\text{-}X_3\text{-}(A_3\text{-}B)\text{-}X_4\text{-}(A_4\text{-}B)\text{-}X_5 \tag{4}$$

$$X_1\text{-}A_1\text{-}B\text{-}X_2\text{-}(A_2\text{-}A_5)\text{-}X_3\text{-}(A_3\text{-}A_6)\text{-}X_4\text{-}(A_4\text{-}A_7)\text{-}X_5 \tag{5}$$

$$X_1\text{-}k\text{-}B\text{-}X_2\text{-}(B)\text{-}X_3\text{-}(B)\text{-}X_4\text{-}(B)\text{-}X_5 \tag{6}$$

(wherein
$X_1$ represents the 1st to 7th amino acid residues in the polypeptide set forth in SEQ ID NO: 1;
$X_2$ represents the 73rd to 177th amino acid residues of the polypeptide;
$X_3$ represents the 178th to 258th amino acid residue of the polypeptide;
$X_4$ represents the 259th to 289th amino acid residue of the polypeptide;
$X_5$ represents the 290 to 334th amino acid residue of the polypeptide;
$A_1$ to $A_7$ represent amino acid sequences set forth in SEQ ID NOS: 2 to 8, respectively; and
B represents an amino acid sequence set forth in SEQ ID NO: 9).

(I-5) The polypeptide according to any one of (I-1) to (I-4), comprising an amino acid sequence set forth in one of SEQ ID NOS: 10 to 14.

(I-6) A polynucleotide encoding at least one of the polypeptides according to (I-1) to (I-5).

(II) Vaccine for Preventing and/or Treating a *Plasmodium falciparum* Infection (II-1) A vaccine for preventing and/or treating a *Plasmodium falciparum* infection, comprising as an active ingredient at least one of the polypeptides according to (I-1) to (I-5).

(II-2) The vaccine according to (II-1), further comprising at least one adjuvant selected from the group consisting of aluminium hydroxide gel, K3 (K-type CpG adjuvant), D35 (D-type CpG adjuvant), and sHZ (synthetic hemozoin adjuvant).

(II-3) The vaccine according to (II-1) or (II-2), further comprising a ligand having innate immune-stimulatory activity.

(II-4) The polypeptide according to any one of (I-1) to (I-5), which is used as a vaccine for preventing and/or treating a *Plasmodium falciparum* infection.

(II-5) A combination of the polypeptide according to one of (I-1) to (I-5) with at least one adjuvant selected from the group consisting of aluminium hydroxide gel, K3 (K-type CpG adjuvant), D35 (D-type CpG adjuvant), and sHZ (synthetic hemozoin adjuvant), the combination being used as a vaccine for preventing and/or treating a *Plasmodium falciparum* infection.

(II-6) A combination of the polypeptide according to one of (I-1) to (I-5) with at least one adjuvant selected from the group consisting of aluminium hydroxide gel, K3 (K-type CpG adjuvant), D35 (D-type CpG adjuvant), and sHZ (synthetic hemozoin adjuvant), and a ligand having innate immune-stimulatory activity, the combination being used as a vaccine for preventing and/or treating a *Plasmodium falciparum* infection.

(II-7) A vaccine for preventing and/or treating a *Plasmodium falciparum* infection, comprising the polypeptide set forth in SEQ ID NO: 1 and an adjuvant.

(II-8) The vaccine according to (II-7), wherein the adjuvant is at least one member selected from the group consisting of K3 (K-type CpG adjuvant), D35 (D-type CpG adjuvant), and sHZ (synthetic hemozoin adjuvant), or a combination of at least one of these adjuvants with aluminium hydroxide gel.

(II-9) The vaccine according (II-7) or (II-8), further comprising a ligand having innate immune-stimulatory activity.

(II-10) A combination of a polypeptide set forth in SEQ ID NO: 1 with an adjuvant, the combination being used as a vaccine for preventing and/or treating a *Plasmodium falciparum* infection.

(II-11) A combination of a polypeptide set forth in SEQ ID NO: 1, an adjuvant, a ligand having innate immune-stimulatory activity, the combination being used as a vaccine for preventing and/or treating a *Plasmodium falciparum* infection.

(II-12) The combination according to (II-10) or (II-11) wherein the adjuvant is at least one member selected from the group consisting of K3 (K-type CpG adjuvant), D35 (D-type CpG adjuvant), and sHZ (synthetic hemozoin adjuvant), or a combination of at least one of these adjuvants with aluminium hydroxide gel.

(III) Diagnostic Agent for a *Plasmodium falciparum* Infection (III-1) An antibody to the polypeptide according to one of (I-1) to (I-5).

(III-2) The antibody according to (III-1) having affinity for polypeptides set forth in SEQ ID NO: 23 to 37.

(III-3) The antibody according to (III-1) having affinity for polypeptides set forth in SEQ ID NO: 23 to 25.

(III-4) A diagnostic agent for a *Plasmodium falciparum* infection, comprising, as an active ingredient, the polypeptide according to one of (I-1) to (I-5), or the antibody according to one of (III-1) to (III-3).

Advantageous Effects of Invention (i) The polypeptide represented by formula (1) (hereinafter sometimes simply referred to as "polypeptide (1)") has high immunogenicity and can maintain high anti-SE36 antibody titers over a long period of time when used as a vaccine. Accordingly, immunity against malaria parasites can be acquired, and the acquired immunity can be maintained for a long period of time.

(ii) According to the polypeptide (1), sufficient immunity can be acquired with a dose that is 1/10th to 1/100th the amount of an antigen polypeptide required to be used to produce an antibody to malaria parasites in vivo. Due to such a small dose, the polypeptide (1) is useful from an economic viewpoint as well.

(iii) The use of the polypeptide (1) as a vaccine can induce an antibody to a protective epitope. Therefore, the polypeptide (1) of the present invention can be used as a malaria vaccine having high immunogenicity (particularly a *Plasmodium falciparum* malaria vaccine).

(iv) According to the present invention, a combination of the polypeptide set forth in SEQ ID NO: 1 (hereinafter sometimes referred to as "polypeptide (2)" or "original SE36 polypeptide") with an optimal adjuvant can be provided. Although the polypeptide (2) itself also has higher antigenicity than a natural SERA polypeptide, a combination of the polypeptide (2) with specific adjuvant or adjuvants can exhibit more remarkable excellent antigenicity. Accordingly, the combined use of the polypeptide (2) with specific adjuvant(s) (e.g., a combination of the polypeptide (2) with a human TLR9 ligand adjuvant, or with aluminium hydroxide gel and a human TLR9 ligand adjuvant, particularly K3 (K-type CpG adjuvant), can induce even higher anti-SE36 antibody titers.

BRIEF DESCRIPTION OF DRAWINGS

FIG. 1-1 shows the amino acid sequences of polypeptide (2) (original SE36 polypeptide) and polypeptides (1) (SE36-1 to SE36-3).

FIG. 1-2 shows the amino acid sequences of polypeptides (1) (SE36-4 to SE36-5) and a negative SE36 polypeptide.

FIG. 1-3 shows the base sequence of a nucleotide encoding the amino acid sequence of the polypeptide (2) (original SE36 polypeptide).

FIG. 1-4 shows the base sequence of a nucleotide encoding the amino acid sequence of the polypeptide (1) (SE36-1).

FIG. 1-5 shows the base sequence of a nucleotide encoding the amino acid sequence of the polypeptide (1) (SE36-2).

FIG. 1-6 shows the base sequence of a nucleotide encoding the amino acid sequence of the polypeptide (1) (SE36-3).

FIG. 1-7 shows the base sequence of a nucleotide encoding the amino acid sequence of the polypeptide (1) (SE36-4).

FIG. 1-8 shows the base sequence of a nucleotide encoding the amino acid sequence of the negative SE36 polypeptide.

FIG. 1-9 shows the amino acid sequence of an epitope mapping polypeptide.

FIG. 2 shows the location and positional relationship between the 8-mer repeat region and the serine-rich region in the polypeptide (2) (original SE36 polypeptide), polypeptides (1) (SE36-1 to 36-5 polypeptides), and negative SE36 polypeptide.

FIG. 3 shows the results of measurement of antibody titers of the whole IgG against SE36 after inoculation of the polypeptide (2) (original SE36 polypeptide), polypeptides (1) (SE36-1 to SE36-5 polypeptides), and negative SE36 polypeptide.

FIG. 4 shows the results of epitope mapping of the polypeptide (2) (original SE36 polypeptide), and polypeptides (1) (SE36-1 to SE36-5 polypeptides) (Test Example 2). In FIG. 4, 1 to 15 on the abscissa show the polypeptides used for mapping 15 epitopes set forth in SEQ ID NO: 23 to 37.

FIG. 5 shows the results of antibody induction by combined use of the polypeptide (2) (original SE36 polypeptide) and adjuvant(s) (aluminium hydroxide gel (Alum) alone, K3 alone, or aluminium hydroxide gel (Alum) and K3).

FIG. 6 is a graph showing changes over time in antibody titers of the whole IgG measured after combined use of various adjuvants (aluminium hydroxide gel (Alum); aluminium hydroxide gel (Alum) and K3; aluminium hydroxide gel (Alum) and D35; and aluminium hydroxide gel (Alum) and sHZ) with the polypeptide (2) (original SE36 polypeptide) versus the use of the polypeptide alone (2) (original SE36 polypeptide).

FIG. 7 is a graph showing the results of epitope mapping in Test Example 3. In FIG. 7, the polypeptides of SEQ ID NO: 23 to 37 used for mapping 15 epitopes are shown as 1 to 15 on the abscissa. Used as adjuvants for the polypeptide (2) were aluminium hydroxide gel (Alum) only (top-left figure), aluminium hydroxide gel and K3 (Alum+K3) (K-type CpG adjuvant) (top-right figure), aluminium hydroxide gel and D35 (D-type CpG adjuvant) (Alum+D35) (bottom-left figure), or aluminium hydroxide gel and sHZ (synthetic hemozoin adjuvant) (Alum+sHZ) (bottom-right figure).

FIG. 8 shows the 14-day measurement results of the number of malaria parasite-infected red blood cells in the blood (parasitemia (%)) measured after immunization of squirrel monkeys with the polypeptide (2) and aluminium hydroxide gel (Alum) (n=2) (left figure); polypeptide (2) (SE36), aluminium hydroxide gel (Alum), and K3 (n=3) (center figure); and aluminium hydroxide gel (Alum) and K3 (n=2) (right figure), after subsequent inoculation with a malaria parasite. In FIG. 8, "dt" indicates ethical death of squirrel monkeys.

DESCRIPTION OF EMBODIMENTS

1. SERA Polypeptide Variant

Figure 2:
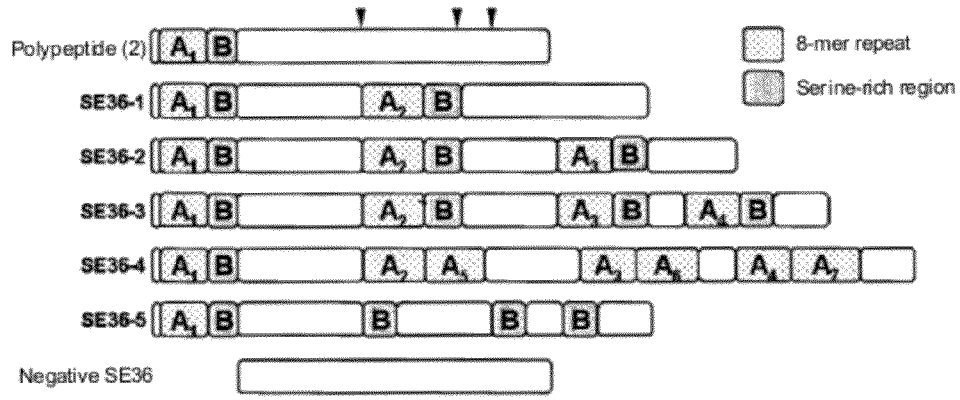

The polypeptides (1) and (2) of the present invention, which are useful as vaccines for malaria parasite infections, are described below in detail. Herein, the polypeptides (1) and (2) may be collectively referred to as "the polypeptide of the present invention".

(1-1) SERA polypeptide

SERA (serine-repeat antigen) is a protein antigen with a molecular weight of 115 kd consisting of 989 amino acids in total and expressed by a Pf gene at the intra-erythrocyte stage. The structure of SERA consists of 3 domains, i.e., 47 kd-50 kd-18 kd, in order of the N-terminal to the C-terminal direction. The SERA working as a precursor for these domains is expressed by 4 exons comprising a total of 5868 bases, processed and cleaved at the intra-erythrocyte stage during merozoite release to yield the above-described domains (Molecular and Biochemical Parasitology, 86, pp. 249-254, 1997; and Experimental Parasitology, 85, pp. 121-134, 1997). In addition, the data on the full length of the SERA gene (DNA) and the amino acid sequence encoded by this gene are open to the public and available from GenBank (Accession Number: J04000; www.ncbi.nlm.nih.gov). The N-terminal region of SERA (hereinafter referred to as "47 kd region") consists of 382 amino acids in total. The homology search between the Pf strains relative to the sequence indicates that SERA is varied since in some regions there is amino acid deletion or addition, or amino acid variation (non-synonymous substitution) at about 20 positions (Molecular and Biochemical Parasitology, supra; and Experimental Parasitology, supra).

(1-2) Polypeptide (2)

Polypeptide (2) is the original SE36 polypeptide set forth in SEQ ID NO: 1.

The polypeptide (2) is derived from an SE47' antigen (Vaccine, 14, pp. 1069-1076, 1996; hereinafter simply referred to as "SE47'"), which is based on a 47-kd region of SERA of the above-described Honduras-1 strain of *Plasmodium falciparum* (Pf) (hereafter simply referred to as "Hond-1"). The polypeptide (2) consists of a total of 334 amino acids, in which the sequence starts from the N-terminal methionine (the 1st amino acid) of 382 amino acids constituting 47 kd of SERA of Hond-1, and in the ordinal number towards the C-terminal, the 16th amino acid codon (aspartic acid) is substituted with an initiation codon (methionine), and a translation stop codon is inserted after the 382nd amino acid (glutamic acid), and further the 33 polymerized serine residues (193rd to 225th serines) occupying the serine repeat region are deleted. The amino acid sequence of the polypeptide (2) is specifically shown as SEQ ID NO: 1 in FIG. 1-1. The polypeptide (2) set forth in SEQ ID NO: 1 has higher immunogenicity than the natural SERA polypeptide.

(1-3) Polypeptide (1)

Polypeptide (1) is an improved SE36 polypeptide obtained by further improving the polypeptide set forth in SEQ ID NO: 1 (2) to have higher immunogenicity.

The polypeptide (1) is represented by the following formula (1):

$$X_1\text{-}A\text{-}B\text{-}X_2\text{-}Y\text{-}X_3\text{-}(Y)n\text{-}X_4\text{-}(Y)n\text{-}X_5 \quad (1)$$

wherein $X_1$ represents the 1st to 7th amino acid residues in the polypeptide set forth in SEQ ID NO: 1;

$X_2$ represents the 73th to 177th amino acid residues of the polypeptide;

$X_3$ represents the 178th to 258th amino acid residues of the polypeptide;

$X_4$ represents the 259th to 289th amino acid residues of the polypeptide;

$X_5$ represents the 290th to 334th amino acid residues of the polypeptide;

Y represents any one selected from A-A, A-B, and B; and n represents an integer of 0 or 1.

In formula (1), A represents an 8-mer repeat sequence contained in a 47-kd region of SERA polypeptide of *Plasmodium falciparum*. In the present invention, any sequence that corresponds to the 8-mer repeat sequence can be used as sequence A, even if there is amino acid variation (non-synonymous substitution) among Pf strains. Examples of amino acid sequences that can be preferably used as sequence A include the following specific sequences $A_1$ to $A_7$ (shown with the N-terminus at the left).

$A_1$: TGESQTGNTGGGQAGNTVGDQAGSTGGSPQGSTGASQPGS (SEQ ID NO: 2)

$A_2$: TGESQTGNTGGGQAGNTGGDQAGSTGGSPQGSTGASPQGSTGASPQGSTGASQPGS (SEQ ID NO: 3)

-continued

```
                                                              (SEQ ID NO: 4)
A₃:  TGESQTGNTGGGQAGNTVGDQAGNTVGDQAGSTGGSPQGSTGASQPGS (SEQ ID NO: 5)
A₄:  TGESQTGNTGGGQAGNTGGGQAGNTVGDQAGSTGGSPQGSTGASQPGS (SEQ ID NO: 6)
A₅:  TGESQTGNTGGGQVGNTGGGQAGSTGGSPQGSTGASQPGSSEPSNPVS (SEQ ID NO: 7)
A₆:  TGESQTGNTGGGQAGNTVGGQAGNTGGGQAGNTGGDPQGSTGGSQPGS (SEQ ID NO: 8)
A₇:  TGESQTGNAGGGQAGNTVGDQAGSTGGSPQGSTGASPQGSTGASPQGSTGASQPGS.
```

In formula (1), A linked to $X_1$ is preferably $A_1$ (SEQ ID NO: 2).

In formula (1), B represents the amino acid sequence of a serine-rich region in the 47-kd region of the SERA polypeptide of *Plasmodium falciparum*. In the present invention, any sequence that corresponds to the amino acid sequence of the serine-rich region can be used as sequence B, even if there is amino acid variation (non-synonymous substitution) among Pf strains. Examples of amino acid sequences that can be preferably used as sequence B include the following specific sequence (shown with the N-terminus at the left)

```
                                               (SEQ ID NO: 9)
      B: SEPSNPVSSGHSVSTVSVSQTSTSS.
```

In formula (1), A and B can be suitably selected from the above specific sequences (SEQ ID NO: 2 to 8, and SEQ ID NO: 9) and used in combination. The amino acid sequence A may be any one selected from the above amino acid sequences shown as $A_1$ to $A_7$. The amino acid sequence of one polypeptide may contain, as the amino acid sequence A, two or more of the same amino acid sequence selected from $A_1$ to $A_7$, or any combination of different amino acid sequences selected from $A_1$ to $A_7$.

Y may be suitably selected from A-A, A-B, and B. Preferably, Y is either A-B or B.

Examples of preferable polypeptides (1) in the present invention include polypeptides (1) set forth in SEQ ID NO: 10 to 14, i.e., SE36-1 to SE36-5. FIG. 2 shows a schematic diagram thereof. As in formula (1), SE36-1 to SE36-5 can be represented by the following formulas:

Formula: $X_1$-A-B-$X_2$-Y-$X_3$-(Y)n-$X_4$-(Y)n-$X_5$

SE36-1: $X_1$-$A_1$-B-$X_2$-($A_2$-B)-$X_3$-(Y)0-$X_4$-(Y)0-$X_5$

SE36-2: $X_1$-$A_1$-B-$X_2$-($A_2$-B)-$X_3$-($A_3$-B)-$X_4$-(Y)0-$X_5$

SE36-3: $X_1$-$A_1$-B-$X_2$-($A_2$-B)-$X_3$-($A_3$-B)-$X_4$-($A_4$-B)-$X_5$

SE36-4: $X_1$-$A_1$-B-$X_2$-($A_2$-$A_5$)-$X_3$-($A_3$-$A_6$)-$X_4$-($A_4$-$A_7$)-$X_5$

SE36-5: $X_1$-$A_1$-B-$X_2$-(B)-$X_3$-(B)-$X_4$-(B)-$X_5$     (1)

(in the above formulas, (Y)0 means that there is no amino acid residue corresponding to Y; that is, (Y)0 indicates a single bond).

Among SE36-1 to SE36-5, SE36-3 to SE36-5 are preferable, SE36-3 and SE36-5 are more preferable, and SE36-3 is particularly preferable.

(1-4) Synthesis of the Polypeptide of the Present Invention

The polypeptide of the present invention can be synthesized by known methods, and the synthesis method is not particularly limited. For example, the polypeptide (2) can be synthesized by the following method. After a DNA fragment (hereinafter sometimes referred to as "SE36 gene (DNA)") encoding the polypeptide (2) is synthesized and cloned, an expression vector for the synthesized gene clone is constructed. The vector is transfected into a host (for example, *Escherichia coli*), and the obtained transformant is cultured.

The expression efficiency of SE36 gene (DNA) having native Pf codons in *Escherichia coli* is low. Therefore, when *E. coli* is used as a host, it is desirable to convert all naturally occurring Pf codons encoding the amino acid sequence of the polypeptide of the present invention into *Escherichia coli* codons to achieve efficient production of the polypeptide as in the present invention.

Although the synthesis of the polypeptide (2) is explained below, the polypeptide (1) can also be synthesized in a similar manner.

Synthesis and Cloning of SE36 Gene (DNA)

Figure 3:
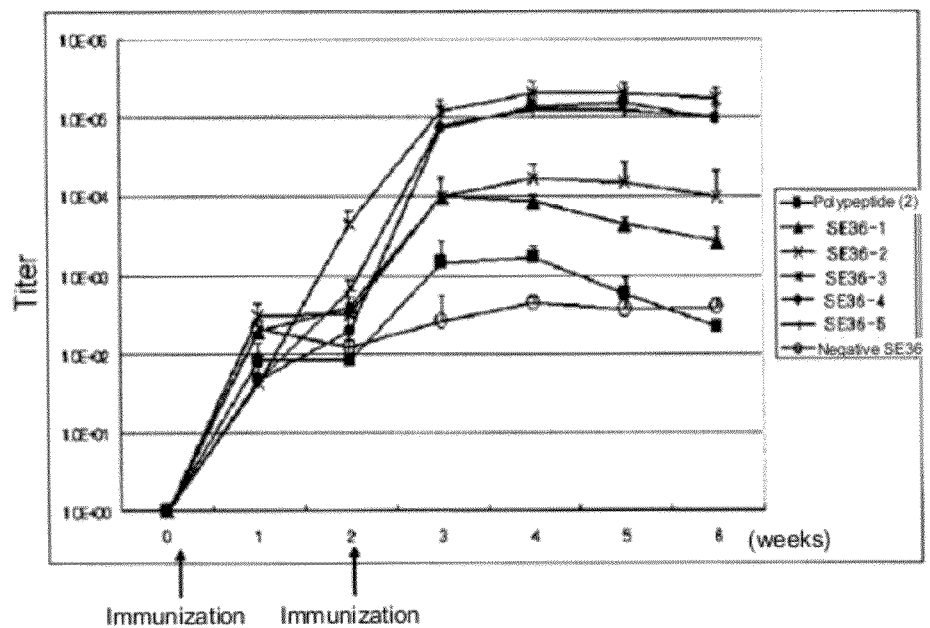

A theoretical base sequence of an SE36 gene (DNA) of Pf (SE36 gene having Pf codons) and an amino acid sequence coded thereby are available from well-known gene database publication organizations, such as DDBJ, GenBank, and EMBL on the Internet. The amino acid sequence of the polypeptide (2) is encoded by the nucleotide sequence set forth in SEQ ID NO: 16 (FIGS. 1 to 3). Accordingly, SE36 gene (DNA) encoding the amino acid sequence (SEQ ID NO: 1) of the polypeptide (2) is synthesized based on SEQ ID NO: 16. For example, DNA encoding the amino acid sequence of the polypeptide (1) is synthesized based on the nucleotide sequences set forth in SEQ ID NO: 17 to 22 that encode the amino acid sequences (SEQ ID NO: 10 to 14) of SE36-1 to SE36-5.

Theoretical conversion of Pf codons into *Escherichia coli* codons may be conducted referring to, for example, the codon usage database of GenBank and publications of the present inventors (the above-mentioned Vaccine; and Molecular Biochemistry of Parasitology, 63, 265-273, 1994). In the conversion into *Escherichia coli* codons, care should be taken to not damage the antigenicity due to non-synonymous substitution of amino acids except for substitution of the N-terminal amino acid with an initiation codon Met, because the native amino acid sequence of naturally occurring Pf is considered to be important.

In the synthesis of DNA, a commercially available DNA synthesizer, such as a DNA/RNA synthesizer (Applied Biosystems Model 392, a product of PE Co., USA) or an ASU-102U DNA synthesizer (a product of Biosset Ltd., USA) can be used. By using such a synthesizer, sense (+) and antisense (−) DNA fragments, in which about 100 to about 200 nucleotides are polymerized, are separately synthesized, and each DNA fragment thus synthesized is purified, for example, by polyacrylamide electrophoresis. Subsequently, a complementary strand (pair) of the purified single-stranded DNA fragment is annealed to give a synthetic double-stranded DNA fragment.

In cloning of the synthetic double-stranded DNA fragment, a known or commercially available cloning vector of which the host is *Escherichia coli* (various vectors disclosed in "Cloning Vectors: A Laboratory Manual", 1-1 to 1-D-1-8, P. H. Pouwels, et al., Elsevier 1988), for example, a combination of a plasmid pBluescript II SK and *E. coli* XL1-BLue (Stratagene, USA) may be used. In such cloning, for example, a restriction enzyme-digested fragment of the above-mentioned DNA fragment is inserted into the restriction enzyme sites of a vector digested with the same enzyme, and the thus constructed vector is transferred to a host to give a transformant clone. Subsequently, each clone containing the double-stranded DNA fragment is amplified by culturing the transformant, and each base sequence can be determined by means of the chain terminator method (dideoxy method) or the Maxam-Gilbert method. In this procedure, a commercially available DNA sequencer, e.g., ABI PRISM 3700 (a product of PE Co., USA), may be used. Based on the results, approximately 5 to 10 clones of double-stranded DNA fragments covering the full length of SE36 gene DNA are selected.

The cloning of the full length of an SE36 gene (DNA) may be achieved by sequentially ligating the aforementioned double-stranded DNA fragments together. For example, when 8 clones (8 pairs) are obtained in the above operation, these double-stranded DNA fragments can be ligated one by one to give a full-length SE36 gene DNA. Then, the full-length DNA is cloned in the same manner as mentioned above. In carrying out the ligation, it is desirable to introduce a cohesive site for ligation by restriction enzymes at both ends of each fragment of the double-stranded DNAs. In such introduction, the codon base sequence(s) has to be adjusted so that the amino acid sequence of the native Pf is not changed. In the polypeptide (1), the cohesive site for ligation by restriction enzymes may remain in the ligation site of the full-length DNA, or may be translated as is and be present in an amino acid sequence.

Construction of Expression System of SE36 Gene

In producing an expression vector for an SE36 gene (DNA), a known or commercially available expression vector of which the host is *Escherichia coli* (variously disclosed in "Cloning Vectors: A Laboratory Manual"; supra), such as, a combination of plasmid pET-3a and *Escherichia coli* BL21 (DL3) pLysS or *Escherichia coli* BL21 (DL3) pLysE (a product of Stratagene, USA) may be used. In producing such a vector, for example, a restriction enzyme-digested fragment containing SE36 gene (DNA) is cut out from the above cloning vector and then inserted into the restriction enzyme site of a vector cleaved with the same enzyme. Alternatively, the expression vector for an SE36 gene may also be prepared from pET-SE47' (Vaccine, supra). In this case, for example, the whole or partial region that encodes the serine repeat region is cleaved by a restriction enzyme from pET-SE47' or an SE47' synthetic gene contained therein, and the expression vector for an SE36 gene is prepared in the same manner as above. Subsequently, the resulting expression vector is transferred to a host to give a transformant. From such transformants, the most appropriate one as an expression system for mass production of the polypeptide SE36 can be screened in view of industrial applicability.

Mass production of the polypeptide of the present invention is achieved by culturing the aforementioned transformant of *Escherichia coli*. In view of enhancement of productivity of the polypeptide of the invention, in such a culture, it is possible to improve or reform a manipulation such as the use of an inducer, e.g., IPTG (isopropyl-1-thio-β-D-galactopyranoside), avoidance of catabolite repression, culture medium composition, culture temperature and period, removal of proteases in host cells, and the like. These may be achieved by alteration of an expression vector, change of a promoter or host organism, etc.

Purification of Polypeptide

When the polypeptide of the present invention is secreted outside the cells, the culture solution after removal of the cells from the aforementioned transformant culture is used as a starting material for extraction of the SE36 polypeptide. When SE36 is accumulated in the cells, the cells may be recovered from the culture, for example, by centrifugation, filtration, etc., and extracted to give the above SE36 polypeptide. At the first step of extraction, the cells may be destroyed by digestion with an enzyme, destruction with osmotic pressure, sudden pressure and decompression, sonication, use of various homogenizers, etc. The destroyed cells are then fractionated by physical means such as low-speed centrifugation, ultra-centrifugation, filtration, a molecular sieve, membrane concentration, etc.; or by chemical means such as a precipitating agent, a solubilizing agent, an adsorbent and desorption agent, a dispersing agent, etc.; or by physicochemical means such as electrophoresis, column chromatography, a support, dialysis, salting-out, etc. These techniques may be used in combination. In applying these techniques, physicochemical conditions, such as temperature, pressure, pH, and ion strength, can be suitably set.

Polypeptide of the Present Invention and Confirmation of its Antigenicity

Detection and size confirmation of the obtained polypeptide of the present invention may be achieved, for example, by determination of sedimentation coefficient, molecular sieve, SDS-polyacrylamide electrophoresis, etc. Antigenicity of the polypeptide of the invention may be confirmed by means of an antigen-antibody reaction using a polyclonal or monoclonal antibody to SERA 47 kd, such as, Western blot analysis, ELISA, agglutination reaction, fluorescent antibody technique, radioimmunoassay, and the like. In addition, immunogenicity of the polypeptide of the present invention and the ability of an anti-SE36 antibody to inhibit Pf parasite growth can be confirmed, for example, by means of an antigen-antibody reaction using the serum of a patient suffering from Pf malaria or an experimental small animal immunized with said polypeptide, such as a rat or mouse, or by growth inhibition (i.e., a neutralization reaction) of Pf merozoites within erythrocytes, or determination of the blood Pf number in an anti-SE36 antibody carrier.

2. Malaria Vaccine

The present invention provides a malaria vaccine comprising the polypeptide of the present invention. Vivax malaria, malariae malaria, ovale malaria, and falciparum malaria are known as malaria parasite infections. The vaccine of the present invention is suitable for use as a falciparum malaria vaccine because it has remarkably high specificity as a falciparum malaria antigen. However, the use of the vaccine is not limited thereto, and the vaccine can be used for other malaria parasite infections.

An example method for preparing a vaccine using the polypeptide (2) is described below. However, a vaccine can also be prepared by using the polypeptide (1) in a similar manner.

(2-1) Preparation of a Vaccine

As an antigen, the polypeptide (2) purified above is dissolved in a solvent, such as isotonic PBS (phosphate buffer saline), to give a vaccine stock solution.

The above antigen for vaccine may be immobilized with a conventional inactivating agent to stabilize the steric structure. Examples of inactivating agents that can be used include formalin, phenol, glutaric dialdehyde, β-propiolactone, and the like, which may be added before or after preparation of the vaccine stock solution. When formalin is used, the amount to be added is about 0.005 to 0.1% (v/v), the inactivation temperature is about 4 to 38° C., and the inactivation period is about 5 to 180 days. If the antigenicity is damaged by inactivation, ingenuity is required to moderate the inactivation conditions. Such moderation may be achieved, for example, by reduction of the amount of inactivating agent used, addition of a neutral or basic amino acid, lowering of the inactivation temperature, etc. Free formaldehyde remaining unchanged after the inactivation step may be, if required, neutralized with addition of an equivalent of sodium hydrogen sulfite or removed by dialysis.

In order to induce mucous or local immunity by oral or nasal inoculation of a vaccine, the polypeptide (2) (i.e., antigen) may be processed or modified. For this purpose, a drug delivery system (DDS) technique using, for example, liposome, emulsion, microcapsules, micro-spheres, polylactic acid, polyglycolic acid, etc., may be applied. The preparation thus obtained is used as a vaccine stock solution in the subsequent step.

The vaccine stock solution is diluted, for example, with the above-mentioned PBS to adjust the amount of the antigen in the vaccine so that antibody production is induced and immunity is established. In this process, it is possible to add a stabilizer for increasing the heat resistance of the vaccine and to add an adjuvant as an auxiliary for enhancing antigenicity. As a stabilizer, for example, sugars or amino acids may be used. Mineral oil, vegetable oil, alum, aluminum compounds (e.g., aluminium hydroxide gel), bentonite, silica, muramyl dipeptide derivatives, thymosin, interleukin, etc., may be used as an adjuvant. Examples of adjuvants that can be preferably used include, as described below, aluminium hydroxide gel and human TLR9 ligand adjuvants. Specific examples of human TLR9 ligand adjuvants include K3 (K-type CpG adjuvant), D35 (D-type CpG ODN adjuvant), and sHZ (synthetic hemozoin adjuvant).

Subsequently, the resulting vaccine is dispensed into vials in an appropriate amount, such as in vials of about 1 to 20 ml, and the vials are tightly closed or sealed for use as vaccine preparations. Such vaccine preparations may be used in a liquid state, or formed into dry preparations by lyophilization after dispensing and used.

(2-2) Assay of Vaccines

Assay of vaccines, which is related to production process control and quality control, is conducted in accordance with the Japanese Rules for "Minimum Requirements for Biological Products" based on the Pharmaceutical Affairs Law (Law No. 145 enacted in 1960), Article 42, Section 1; WHO recommendation on "Requirements for Biological Substances" (WHO Technical Report Series (TRS), No. 889, pp. 105 to 111, 1999), etc. A malaria vaccine has not yet been put to practical use, and there is no standard for pharmaceutical preparations. The assay, therefore, may be conducted in accordance with a standard for an analogous vaccine, such as the variety of rules on safety and efficacy as described in WHO recommendation on "Requirements for Hepatitis B Vaccines Made by Recombinant DNA Techniques" (the aforementioned TRS, No. 786, 1898, and No. 889, 1999), and "Requirements for Japanese Encephalitis Vaccine (Inactivated) for Human Use" (the aforementioned TRS, No. 771, 1988), etc. For example, the assay for sterilization, denial of abnormal toxicity, protein content, purity, hydrogen ion concentration, confirmation of antigens, antigenic polypeptides, and the like may be conducted in accordance with the rules for a variety of required or recommended tests. A product lot that has passed all of the above tests may be put to practical use as a qualified malaria vaccine preparation.

(2-3) How to Use the Vaccine

The vaccine can be inoculated according to methods common in the art, and the method of vaccine inoculation is not particularly limited. For example, the vaccine can be subcutaneously inoculated at a dose of about 0.25 to 0.5 ml. Such inoculation may be preferably performed 1 to 3 times at intervals of about 2 to 4 weeks.

3. Adjuvants and Vaccine Comprising a Combination of the Adjuvants (3-1) In preparation of the vaccine, the polypeptide (1) may be used together with a combination of known adjuvants. Such adjuvants are not particularly limited, and any adjuvant that can enhance the immunizing effect of the present invention can be used. Examples of usable adjuvants include aluminium hydroxide gel and human TLR9 ligand adjuvants such as K3 (K-type CpG adjuvant), D35 (D-type CpG ODN adjuvant), and sHZ (synthetic hemozoin adjuvant). In addition to these adjuvants, ligands having innate immune-stimulatory activity can also be used as adjuvants.

In the present invention, adjuvants may be used singly or in combination of two or more selected from such adjuvants. Aluminium hydroxide gel has the property of forming an insoluble antigen-adjuvant complex. Due to local accumulation of this antigen-adjuvant complex, combined use of aluminium hydroxide gel with other adjuvant(s) as mentioned above is preferable.

(3-2) In preparation of the vaccine, the polypeptide (2) may also be used together with known adjuvants as exemplified above. Examples of adjuvants that can be preferably used include K3 (K-type CpG adjuvant), D35 (D-type CpG ODN adjuvant), and sHZ (synthetic hemozoin adjuvant), which are human TLR9 ligand adjuvants. However, when the polypeptide (2) is used with a specific combination of adjuvants, particularly excellent effects can be achieved.

Examples of combinations of adjuvants with which the polypeptide (2) can provide particularly excellent immunogenicity include, in addition to combinations of the above-mentioned humans TLR9 ligand adjuvants, (a) a combination of aluminium hydroxide gel and K3 (K-type CpG adjuvant), (b) a combination of aluminium hydroxide gel and D35 (D-type CpG adjuvant), and (c) a combination of aluminium hydroxide gel and sHZ (synthetic hemozoin adjuvant). Among these, (a) a combination of aluminium hydroxide gel and K3 (K-type CpG adjuvant) can maintain high anti-SE36 antibody titers for a long period of time. Accordingly, use of the polypeptide (2) with a combination of specific adjuvants as mentioned above is effective as a malaria vaccine.

4. Diagnostic Agent

The antibody to the polypeptide (1) or (2) can be used for the diagnosis of malaria parasite infections. More specifically, the present invention can provide a diagnostic agent for malaria parasite infections, comprising an antibody to the polypeptide (1) or (2) as an active ingredient. The antibody to the polypeptide (1) or (2) can be obtained, for example, by intraperitoneally, subcutaneously, or intramuscularly inoculating the polypeptide (1) or (2) to an animal, such as a rabbit, guinea pig, or mouse, to generate an antibody and isolate the antibody from the serum of the animal. Such an antibody can be used for detection of an antigen. If the antigen is detected in a sample, for example, serum, of a patient suspected of a malaria parasite infection, the patient can be diagnosed as being infected with a malaria parasite.

An anti-SE36 antibody can be detected by a precipitation reaction, agglutination reaction, neutralization reaction, fluorescent antibody technique, enzyme immunoassay, radioimmunoassay, or the like, using the polypeptide (1) or (2) as an antigen and using the serum, etc., of a patient suspected of a malaria parasite infection as a sample. Accordingly, if the antigen is detected in the sample, the patient is diagnosed as being infected with a malaria parasite.

The antigen and antibody used in diagnosis according to the present invention may be diluted with a solvent, such as the above-mentioned PBS, so that the content of the antigen and antibody in the diagnostic agent becomes the amount necessary for the antigen/antibody reaction.

5. Method for Preventing and/or Treating Malaria Parasite Infections

The vaccine of the present invention has high antibody titers as mentioned above. Therefore, malaria parasite infections can be effectively prevented by pre-administering the vaccine to a subject, such as person in need of prevention against malaria parasite infection.

Because the vaccine of the present invention is particularly effective against *Plasmodium falciparum* infections, *Plasmodium falciparum* infections can be effectively treated by administering the vaccine to a patient infected with *Plasmodium falciparum*. Thus, the present invention further provides a method for preventing and/or treating malaria using a malaria vaccine. The malaria vaccine preparation method, dosage, etc., are as described above.

As described above, administration of the polypeptide (1) or (2) of the present invention together with adjuvants as mentioned above can further enhance malaria preventive and/or therapeutic effects.

EXAMPLES

The present invention is described below in more detail with reference to Test Examples. However, the scope of the invention is not limited to these Examples.

Test Example 1

The present inventors previously concluded from the results of epitope mapping directed to SE36 (SEQ ID NO: 1) that either one of or both of the 8-mer repeat and serine-rich regions that are present in the N-terminal region are important as protective epitopes. (The document that discloses this will be described here.)

Based on the above finding, five kinds of polypeptide (1) (SEQ ID NO: 10 to 14), each containing a plurality of these regions, were designed in this Test Example. At the same time, an original SE36 polypeptide (polypeptide (2): SEQ ID NO: 1), and SE36 without the N-terminal region (negative SE36: SEQ ID NO: 15) as a negative control were designed. FIGS. 1-1 to 1-2 show the amino acid sequences of these polypeptides. FIGS. 1-3 to 1-9 (SEQ ID NO: 16 to 22) show the base sequences of nucleotides encoding the amino acid sequences. FIG. 2 shows a schematic diagram of the structures of five kinds of polypeptide (1), polypeptide (2), and negative SE36 polypeptide.

The method for preparing the polypeptides used in Test Example 1 is described below. Although a method of preparing the polypeptide (2) is described in detail, other polypeptides can also be produced in a similar manner.

Construction of Polypeptide Expression System

The expression system of the polypeptide (2) (SEQ ID NO: 1) was constructed in the following manner.

The DNA base sequence of the full-length SE36 gene that had been theoretically converted from Pf codons to *Escherichia coli* codons was divided into 8 fragments. For each divided fragment, a sense (+) strand and an antisense (−) strand were synthesized to obtain 16 single-stranded DNA fragments in total (8 pairs), which were annealed to give 8 pairs of double-stranded DNA. These sequences were ligated to each other to give a full-length of SE36 gene, from which an expression vector was constructed.

In this operation, the basic procedure for cloning and ligation of the synthetic DNA fragments was conducted in accordance with the method of Sambrook et al. (Molecular Cloning: A Laboratory Manual, 2nd edition, Cold Spring Harbor Laboratory Press, 1989).

The above single-stranded DNA fragments were individually synthesized using an Applied Biosystems Model 392 DNA/RNA synthesizer (a product of PE Co., USA). These synthesized fragments were purified by electrophoresis on 10% (w/v) polyacrylamide (containing 50 mM Tris-borate salt, pH 8.3, 1 mM EDTA, and 8M urea). Then, 20 pmoles of the + and − complementary strands of each purified DNA fragment were mixed, and then heated in a buffer solution (20 µl of 20 mM Tris-HCl, pH 7.0, 50 mM NaCl, and 2 mM $MgCl_2$) at 85° C. for 5 minutes.

Further, the complementary regions of both the strands above were annealed by lowering the temperature to 55° C. at a rate of 5° C./5 minutes and then to 25° C. at a rate of 5° C./10 minutes using a Zymoreactor II (a product of ATTO Co., Japan). After annealing, an equal amount of a buffer solution (20 mM Tris-HCl, pH 7.8, 10 mM $MgCl_2$, 5 mM dithiothreitol (DTT), 1 mM each of 4 species of nucleoside-5'-triphosphate (NTP), and 3 units of T4 DNA polymerase) was added, and the mixture was kept at 4° C. for 5 minutes, 25° C. for 5 minutes, and then at 37° C. for 120 minutes.

For construction of SE36 gene, the resulting double-stranded DNA fragments were individually digested with restriction enzymes KpnI and BamHI, and then cloned and multiplied with pBluescript II SK+ and *Escherichia coli* XL1-Blue. The base sequences of the above DNA fragments in each of the clones were determined by the dideoxy method, and 8 clones covering the full length of SE36 gene were screened. The synthesized double-stranded DNA fragments of these 8 clones (8 pairs) were ligated to give a full length of SE36 double-stranded DNA.

In this operation, using a base sequence designed in such a manner that the amino acid sequence of the native Pf was not altered, the restriction enzyme sites for ligation were introduced to both ends of each pair of DNA. Subsequently, the full length of an SE36 gene was cloned with pBluescript II SK+, and then transfected to *Escherichia coli* XL1-Blue for proliferation. The base sequence was determined by the dideoxy method. The results are shown in SEQ ID NO: 10 in the Sequence Listing.

Subsequently, the fragments of the above clone digested with restriction enzymes NdeI and BamHI were inserted and ligated into the NdeI-BamHI cleavage sites of a plasmid pET-3a to construct a SE36 expression vector pET-SE36. This expression vector was transfected to *Escherichia coli* BL21 (DE3) pLysS to give a transformant, *Escherichia coli* BL21 (DE) pLysS/pET-SE37, which was designated as *Escherichia coli* BL/SE36.

Expression and Purification of the Polypeptide

The *Escherichia coli* BL/SE36 obtained above was incubated on an LB medium (Bacto-trypton 1% (w/v), Bactoyeast extract 0.5% (w/v), and NaCl 1% (w/v)) containing 50 µg/ml of ampicillin at 37° C. for 18 hours to give seeds. The seeds (50 ml) were inoculated on fresh LB medium (5 L) and incubated at 37° C. When the number of cells reached $1 \times 10^8$/ml, IPTG (isopropyl-β-D-thiogalactopyranoside) was added at a final concentration of 50 µg/ml, and further incubated at 37° C. for 3 hours. After the incubation, the mixture was centrifuged (5,000 rpm, 10 minutes) to collect the cells. 3.2 g of cell paste was obtained. The paste was suspended into 9.6 ml of an ice-cold lysis buffer solution (50 mM Tris-HCl, pH 8.0, and 1 mM EDTA). Then, the procedures (1) to (6) were conducted at 4° C. in the order as described.

(1) Sonication

The above cell paste was disrupted by treatment with ultrasonic waves (19.5 kHz, 50 W) 6 times for 20 seconds. The supernatant after centrifugation (15,000 rpm, 30 minutes) was collected and placed in a beaker of 20-ml volume.

(2) Salting-Out with Ammonium Sulfate (I)

To the supernatant in the beaker was added 2.37 g of $(NH_4)_2SO_4$ crystals with stirring to achieve a saturation of 35% (W/W). The mixture was further stirred for 30 minutes for salting-out. Subsequently, the mixture was centrifuged (12,000 rpm, 10 minutes), and the supernatant was discarded. The precipitate was suspended in 9 ml of an ice-cold ammonium sulfate solution (a lysis buffer solution as described above containing 1.1 M $(NH_4)_2SO_4$) at an ammonium sulfate saturation of 30% (w/w). The resulting suspension was centrifuged (12,000 rpm, 10 minutes) and the supernatant was discarded. The precipitate was suspended again into 8.8 ml of a lysis buffer solution (50 mM Tris-HCl (pH 8.0), 1 mM EDTA, 50 mM 2-mercaptoethanol, 9 M urea, and 1% (w/v) TWEEN 80(polysorbate 80)) and recovered. Half the volume (4.4 ml) of the recovered suspension was heated at 60° C. for 10 minutes, then again ice-cooled and filtered through a 0.45-µm filter (a product of Millipore, USA).

(3) Column Purification (I)

The filtrate was chromatographed on a column of SEPHACRYL S-300 (26/60) (gel filtration media) equilibrated with a GF buffer solution (50 mM Tris-HCl (pH 8.0), 1 mM EDTA, 50 mM 2-mercaptoethanol, and 8M urea) (3.5 ml/fraction; flow rate=0.3 ml/minute; 4° C.). Each of the fractions 22-43 was subjected to SDS-polyacrylamide electrophoreses. Based on their migration patterns, the fractions 32-37 containing a large amount of SE36 protein were pooled. The remaining resuspended solution (4.4 ml) was also treated in the same manner as above, then combined with the pooled fractions above, and used in the subsequent operation (4).

(4) Column Purification (II)

The resulting pooled fractions were kept at room temperature, and $(NH_4)_2SO_4$ was added thereto with stirring at an amount of 0.093 g per ml of the pooled fractions to achieve a final ammonium sulfate concentration of 0.7 M. On the other hand, an aqueous column with 13 ml of OCTYL SEPHAROSE (agarose beads, a product of Pharmacia Biotech) was equilibrated with a 10-fold volume of an HIC buffer solution (a GF buffer solution as mentioned above containing 0.7 M $(NH_4)_2SO_4$). The ammonium sulfate-adjusted pooled fractions were poured onto the column at a rate of 0.5 ml/minute. Subsequently, the HIC buffer solution was added to the column until the absorbance decreased, and then for confirmation, the column was eluted with a GF buffer solution that does not contain $(NH_4)_2SO_4$ to elute the adsorbed components. The fractions not adsorbed on the column were placed in a dialysis bag and dialyzed against 1 L of 20-mM Tris-HCl buffer solution (pH 8.0) (containing 1 mM EDTA) at 4° C. for 10 hours. During the dialysis, this outside solution was changed twice.

(5) Salting-Out with Ammonium Sulfate (II)

The dialysis bag after completion of the dialysis was further dialyzed against 0.3 L of a 50% (w/w) saturated $(NH_4)_2SO_4$ solution (containing 20 mM Tris-HCl (pH 8.0) and 1 mM EDTA) at 4° C. for 10 hours to obtain proteins as a precipitate. The precipitate was collected by centrifugation (12,000 rpm, 10 minutes) and suspended into 2 ml of GF buffer solution.

(6) Column Purification (III)

The suspension obtained above was heated at 60° C. for 10 minutes and then cooled back to 4° C. This was filtered through a 0.45-µm filter. The filtrate was chromatographed on a column of the above-mentioned S-300 (26/60) equilibrated with a GF buffer solution 2 (10 mM Tris-HCl (pH 8.0), 1 mM EDTA, 20 mM 2-mercaptoethanol, and 8 M urea) at a flow rate of 0.3 ml/minute. In the same manner as in the above item (3), each fraction was applied to SDS-polyacrylamide electrophoresis to screen fractions of the SE36 protein, which were collected to pool 12 ml fraction. This fraction was added to a dilution buffer (10 mM Tris-HCl (pH 8.0), 1 mM EDTA, and 2 M urea) with stirring so as to give a solution of the SE36 protein at a concentration of 25 µg/ml. The diluted solution was dialyzed against 2 L of PBS (9 mM $NaHPO_4$, 3 mM $NaH_2PO_4$, and 137 mM NaCl (pH 7.4)) at 4° C. for 10 hours. During this operation, the outside solution was changed twice. Subsequently, the inside solution after dialysis was concentrated with CENTPREP 30 (centrifugal filter unit), and filtered through a Durapore 0.22 µm-filter (a product of Millipore, USA) for sterilization to give 10 ml sterile specimen containing 1 mg/ml of the SE36 protein. This was stored as a stock solution for an SE36 vaccine at 4° C.

Determination of the Amino Acid Sequence

The amino acid sequence of the polypeptide (2) thus obtained was determined by Edman degradation using an Applied Biosystems 473A protein sequencer (a product of PE Co., USA). The polypeptide (2) was confirmed to have the amino acid sequence set forth in SEQ ID NO: 1.

Test Example 2

Using the polypeptides (1) (SE36-1 to SE36-5 polypeptides), polypeptide (2), and negative SE36 polypeptide as antigens, a test was performed in the following manner.

Mice were immunized with each of the purified polypeptides (antigens), and induction of antibody titers was monitored. More specifically, thirty-five C57BL/6_tlr4KO mice were divided into 7 groups of 5 mice each, and each group was inoculated with a mixture of one antigen with aluminium hydroxide gel and a K3 adjuvant by subcutaneous injection. FIG. 3 shows the results.

The immunizing amount was defined as 13 µg of aluminium hydroxide gel and 50 µg of K3 per µg of the antigen. As indicated by an arrow in FIG. 3, a second immunization was performed two weeks after the first immunization. Every week, the blood was sampled to obtain the serum, and anti-SE36-IgG antibody titers were determined by an ELISA assay. The ELISA assay was performed in the following manner.

Preparation of ELISA Plate

SE36 was diluted to 1 µg/ml with a coating buffer (pH 9.6, containing 3.4 g of $Na_2CO_3$ and 5.7 g of $NaHCO_3$ in 1 L of distilled water). The diluted SE36 was dispensed into each well of a 96-well MaxiSorp NUNC-Immuno plate (442404: Nunc) using 100 µl per well. The plate was washed twice with a wash buffer (PBS(−) containing 0.05% TWEEN 20 (polysorbate 20)), and then blocked with a blocking buffer (5% skim milk and PBS(−) containing 0.05% Tween 20) and incubated at 4° C. for 2 hours. The blocked ELISA plate was washed with washing buffer 4 to 5 times and stored at −20° C. until use.

Reaction with Test Sera (a) Standard Serum

Plates with 12 (row)×8 (column) wells were used. A blocking buffer was dispensed into each well of the first row in an amount of 150 µl, and into each well of the subsequent rows in an amount of 100 µl. 1.5 µl of a standard serum was placed into the wells of the first row, and the serum and the blocking buffer were mixed thoroughly (1/100 dilution). 50 µl each well of the first row was transferred to the wells of the adjacent row and mixed thoroughly (1/3 dilution). This operation was repeated until the wells of the last row (whereby the serum can be serially diluted to 1/100, 1/300, 1/900, 1/2700, etc.).

(b) Test Sera

Each sample (serum) was diluted with the blocking buffer (to 1/100, 1/500, 1/1000, etc.: the sample was diluted in such a manner that the O.D. values fell within the standard curve). The diluted sample was dispensed into each well in an amount of 100 µl per well. The sample was incubated at room temperature for 2 to 3 hours, or at 4° C. overnight, and then washed with the wash buffer 4 to 5 times.

Reaction with a Secondary Antibody

The secondary antibody (Anti-Mouse IgG (Goat Anti-Mouse IgG (H+L))) (1031-05: SouthernBiotech) was diluted with a blocking buffer to a dilution factor. The resulting mixture was dispensed in an amount of 100 µl per well and incubated at room temperature for 2 to 3 hours, or at 4° C. overnight, followed by washing with the wash buffer 4 to 5 times. The dilution factor of the second antibody can be set as desired.

Detection

TMB (3,3',5,5'-tetramethylbenzidine: Sigma: T8665-100ML), which is a chromogenic substrate, was dispensed in an amount of 50 µl per well. When the sample had turned an appropriately dark blue, 1 mol/l sulfuric acid (Nacalai Tesque: 95626-06) was dispensed in an amount of 50 µl per well. Detection was performed at 450 nm using a plate reader, and background was subtracted at 540 nm.

As shown in FIG. 3, all the polypeptides (1) (SE36-1 to SE36-5) provided higher antibody titers than the polypeptide (2). In particular, SE36-3 to SE36-5 induced high antibody titers. These results indicate that the polypeptide (1) of the present invention, i.e., an improved SE36 polypeptide, can induce an anti-SE36 antibody several ten to several hundred times higher than the amount induced by the polypeptide (2).

Epitope Mapping

Figure 4:
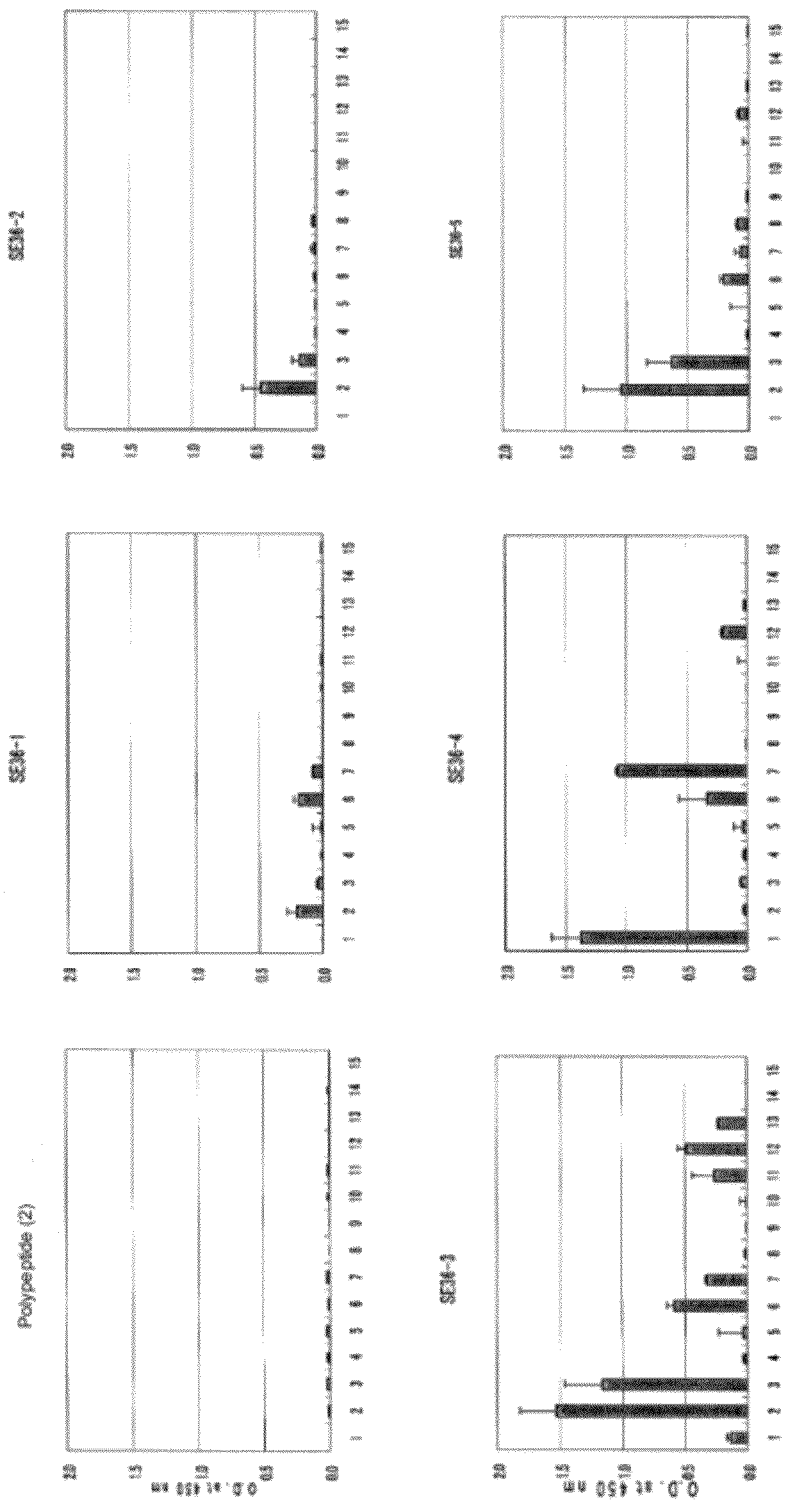

Epitope mapping was performed using the serum obtained in the 4th week. For the epitope mapping, the wells of plates were coated with fifteen peptides set forth in SEQ ID NOS: 23 to 37 at a concentration of 0.03 mM (see FIGS. 1 to 9), and the ELISA assay was performed. FIG. 4 shows the results. The results of epitope mapping indicate that the polypeptides (1) (SE36-1 to SE36-5) highly promote induction of an antibody to the N-terminal region that is important as a protective epitope.

More specifically, induction of the antibody to the N-terminal region of a SE36 polypeptide by using the polypeptide (2) (original SE36 polypeptide) as an antigen is as shown in the upper-left graph of FIG. 4. The results of FIG. 4 show that the polypeptides (1), i.e., SE36-1 to SE36-5 (particularly SE36-3 to SE36-5) can remarkably enhance the induction of the antibody to the N-terminal region of a SE36 polypeptide (epitope polypeptides 1 to 3 (polypeptides set forth in SEQ ID NOS: 23 to 25)).

Test Example 3

As shown below, adjuvants (aluminium hydroxide gel, K3 (K-type CpG adjuvant), D35 (D-type CpG adjuvant), and sHZ (synthetic hemozoin adjuvant) were used in combinations, and their immunogenicity-enhancing effects on the polypeptide (2) were evaluated.

(1) Enhancement of Antibody Induction Capacity by Combined Use of Adjuvants

Figure 5:
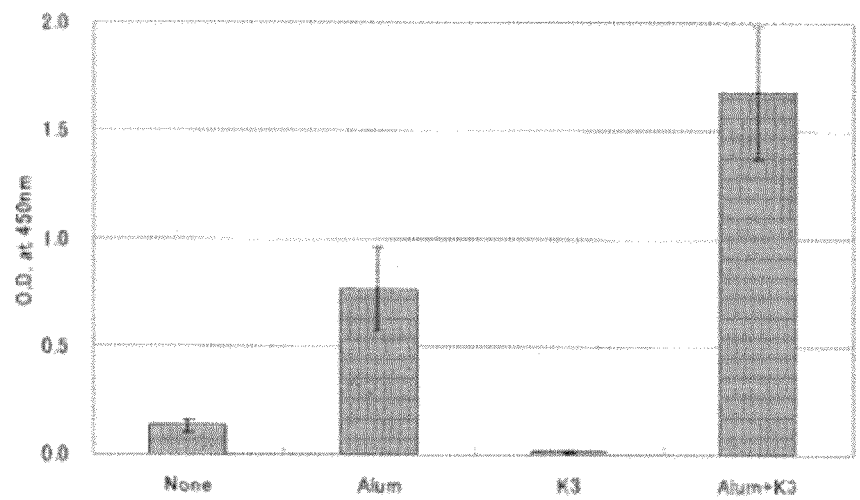

Immunization was performed using the polypeptide (2) alone as the antigen or using the polypeptide (2) with aluminium hydroxide gel, the polypeptide (2) with K3, or the polypeptide (2) with aluminium hydroxide gel and K3. The test method was performed in the same manner as in Test Example 2. Four weeks after the first immunization, anti-SE36-IgG antibody titers were measured. Table 5 shows the results. The results of FIG. 5 show that the combined use of aluminium hydroxide gel and K3 as adjuvants (indicated as "Alum+K3" in FIG. 5) can remarkably induce an anti-SE36 antibody as compared to using the antigen alone (indicated as "none" in FIG. 5), using only aluminium hydroxide gel as the adjuvant (indicated as "Alum" in FIG. 5), and using only K3 as the adjuvant (indicated as "K3" in FIG. 5).

(2) Enhancement of Antibody Induction Capacity by Combined Use of Adjuvants

The present inventors further evaluated the enhancement of immunogenicity of the polypeptide (2) by adjuvants other than the combination of aluminium hydroxide gel and K3. In this test, antibody titers in test animals were evaluated over a long period of time. The specific test method is as shown below.

Twelve cynomolgus monkeys were divided into 4 groups of 3 monkeys. The monkeys were immunized by subcutaneous injection using the following as adjuvants for the polypeptide (2): aluminium hydroxide gel only; aluminium hydroxide gel and K3 (K-type CpG adjuvant); aluminium hydroxide gel and D35 (D-type CpG adjuvant); and aluminium hydroxide gel and sHZ (synthetic hemozoin adjuvant).

Figure 6:
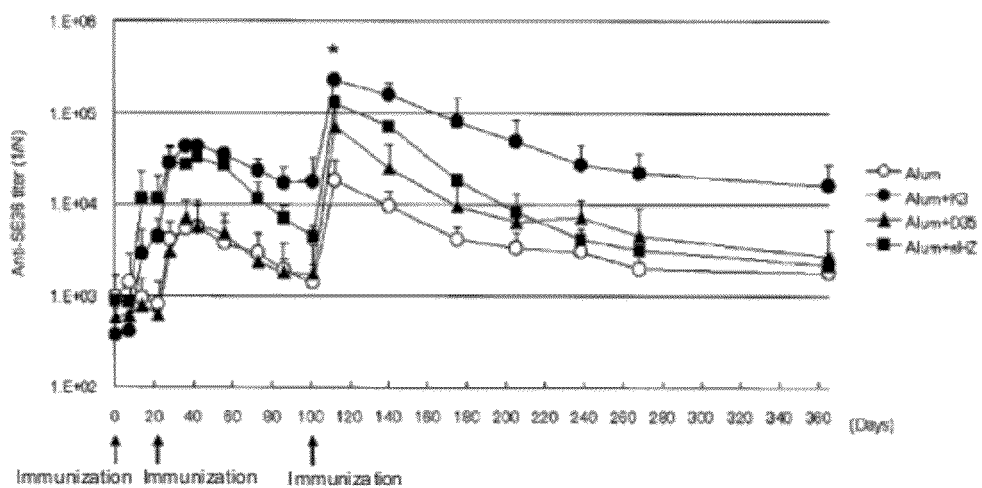

For the immunization, vaccines prepared by adding 500 µg of either K3 or D35, or 1.5 mM sHZ to the polypeptide (2) (10 µg) and aluminium hydroxide gel (125 µg) were used. Immunization was performed at the time points indicated by arrows in FIG. 6 (day 0, day 22, and day 101). On days 0, 7, 14, 22, 28, 36, 42, 56, 73, 86, 101, 112, 140, 175, 205, 238, 268, and 365, blood was drawn, and the serum was collected. The anti-SE36-IgG antibody titers in the serum were measured by an ELISA assay. The ELISA assay was performed in the same manner as in Test Example 2. In Test Example 3, anti-monkey IgG (whole molecule)-peroxidase, antibody produced in a rabbit (A2054: Sigma), was used as a second antibody. FIG. 6 shows the results.

The results of this test show that compared to the use of aluminium hydroxide gel alone, combined use of aluminium hydroxide gel with K3 (K-type CpG adjuvant), D35 (D-type CpG adjuvant), or sHZ (synthetic hemozoin adjuvant) can enhance the immunogenicity of the polypeptide (2), and that in particular, combined use of aluminium hydroxide gel with K3 can provide high antibody titers and also maintain this effect over a long period of time.

Epitope Mapping

Epitope mapping was performed using the sera with the highest antibody titers (indicated with an asterisk (*) in FIG.

Figure 7:
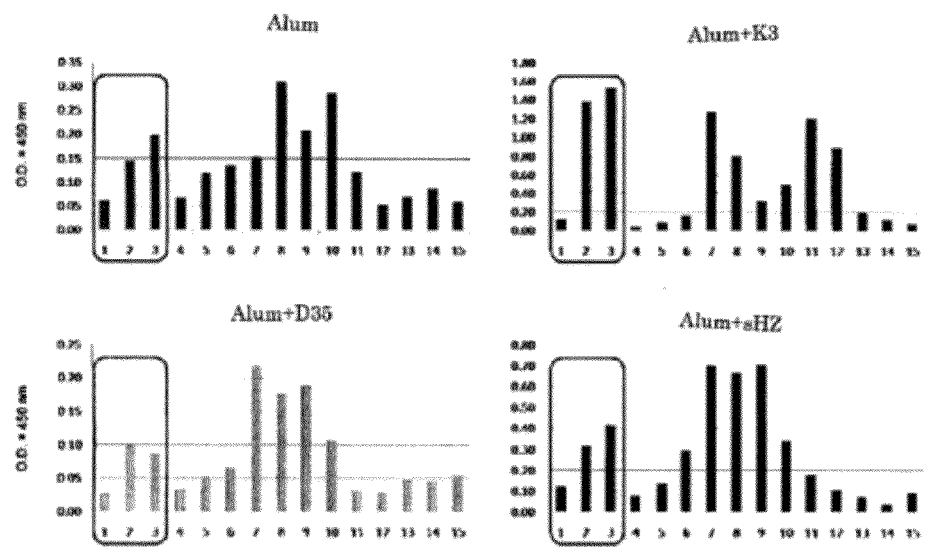

6). For the epitope mapping, the wells of the plates were coated with fifteen peptides shown in FIGS. 1 to 9 (SEQ ID NOS: 23 to 37) (concentration: 0.03 mM) and subjected to the ELISA assay. A comparison was made using one animal having the highest antibody titer in each group. The results show that addition of K3 (K-type CpG adjuvant) can promote antibody titers to the N-terminal region (FIG. 7: circled portions).

The results of this Test Example suggest that addition of a TLR9 ligand adjuvant (K3 (K-type CpG adjuvant), D35 (D-type CpG adjuvant), or sHZ (synthetic hemozoin adjuvant)) can enhance the immunogenicity of the polypeptide (2), and the preparation containing a TLR9 ligand adjuvant can be used as a more effective malaria vaccine.

In the above Test Example, the vaccinated animals were all healthy, and no unusual weight loss; abnormality in behavior, excrement, or appearance; or death was observed. More specifically, safety of the vaccine used in this Test Example was confirmed.

Test Example 4

Squirrel monkeys were immunized with a combination of the polypeptide (2) with adjuvants (aluminium hydroxide gel and K3 (K-type CpG adjuvant)), and the protective effects against malaria parasite were evaluated.

Seven squirrel monkeys were randomly divided into three groups. Each of the three groups of squirrel monkeys was immunized by subcutaneous injection with polypeptide (2) and aluminium hydroxide gel (n=2); polypeptide (2), aluminium hydroxide gel and K3 (n=3) (K-type CpG adjuvant); or aluminium hydroxide gel and K3 (n=2) (K-type CpG adjuvant) twice at three-week intervals. The immunization was performed in such a manner that the total dosage of the components, i.e., (polypeptide (2) (10 µg), aluminium hydroxide gel (125 µg), and K3 (500 µg)), was 0.5 ml. After the immunization, a live malaria parasite was inoculated in a concentration of $5 \times 10^8$ via the femoral vein. The number of malaria parasite-infected red blood cells in each squirrel monkey was determined every day for 14 days.

Figure 8:
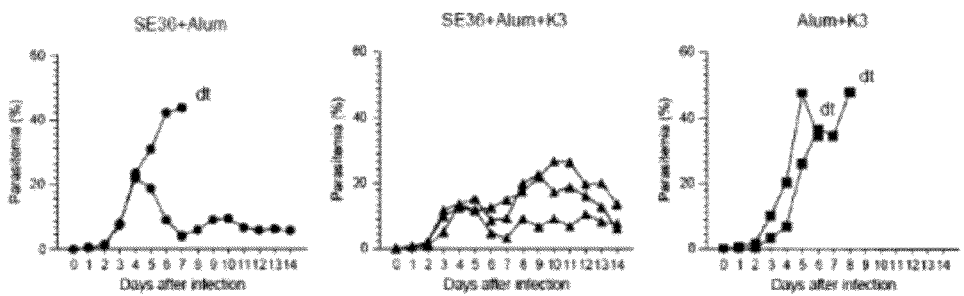

FIG. 8 shows the results. In one of the monkeys (n=2) in the group administered with polypeptide (2) and aluminium hydroxide gel, and both monkeys (n=2) in the group administered with aluminium hydroxide gel and K3, the number of malaria parasite-infected red blood cells reached as high as about 40 to 50%, and these monkeys died ethically by day 9, as shown in FIG. 8. In contrast, in all three monkeys in the group administered with polypeptide (2), aluminium hydroxide gel, and K3 (n=3), the number of malaria parasite-infected red blood cells was lower than 30%, and none of the monkeys in this group died.

These results show that compared to the use of aluminium hydroxide gel alone, combined use of K3 (K-type CpG adjuvant) with aluminium hydroxide gel can more effectively enhance the immunogenicity of the polypeptide (2) and inhibit the growth of the malaria parasite, thus preventing the death of infected subjects.

[Sequence Listing Free Text]

SEQ ID NO: 1 is the amino acid sequence of polypeptide (2).
SEQ ID NO: 2 is the amino acid sequence of $A_1$.
SEQ ID NO: 3 is the amino acid sequence of $A_2$.
SEQ ID NO: 4 is the amino acid sequence of $A_3$.
SEQ ID NO: 5 is the amino acid sequence of $A_4$.
SEQ ID NO: 6 is the amino acid sequence of $A_5$.
SEQ ID NO: 7 is the amino acid sequence of $A_6$.
SEQ ID NO: 8 is the amino acid sequence of $A_7$.
SEQ ID NO: 9 is the amino acid sequence of B.
SEQ ID NO: 10 is the amino acid sequence of an SE36-1 polypeptide.
SEQ ID NO: 11 is the amino acid sequence of an SE36-2 polypeptide.
SEQ ID NO: 12 is the amino acid sequence of an SE36-3 polypeptide.
SEQ ID NO: 13 is the amino acid sequence of an SE36-4 polypeptide.
SEQ ID NO: 14 is the amino acid sequence of an SE36-5 polypeptide.
SEQ ID NO: 15 is the amino acid sequence of a negative SE36-6 polypeptide.
SEQ ID NO: 16 is the base sequence of a nucleotide encoding the amino acid sequence of polypeptide (2).
SEQ ID NO: 17 is the base sequence of a nucleotide encoding the amino acid sequence of an SE36-1 polypeptide.
SEQ ID NO: 18 is the base sequence of a nucleotide encoding the amino acid sequence of an SE36-2 polypeptide.
SEQ ID NO: 19 is the base sequence of a nucleotide encoding the amino acid sequence of an SE36-3 polypeptide.
SEQ ID NO: 20 is the base sequence of a nucleotide encoding the amino acid sequence of an SE36-4 polypeptide.
SEQ ID NO: 21 is the base sequence of a nucleotide encoding the amino acid sequence of an SE36-5 polypeptide.
SEQ ID NO: 22 is the base sequence of a nucleotide encoding the amino acid sequence of a negative SE36 polypeptide.
SEQ ID NO: 23 to 37 are the amino acid sequences of epitope mapping polypeptides 1 to 15.

The invention claimed is:

1. A polypeptide as set forth in formula (1):

$$X_1\text{-}A\text{-}B\text{-}X_2\text{-}Y\text{-}X_3\text{-}(Y)n\text{-}X_4\text{-}(Y)n\text{-}X_5 \quad (1)$$

wherein $X_1$ represents the 1st to 7th amino acid residues in a polypeptide set forth in SEQ ID NO: 1;

$X_2$ represents the 73th to 177th amino acid residues of the polypeptide set forth in SEQ ID NO: 1;

$X_3$ represents the 178th to 258th amino acid residues of the polypeptide set forth in SEQ ID NO: 1;

$X_4$ represents the 259th to 289th amino acid residues of the polypeptide set forth in SEQ ID NO: 1;

$X_5$ represents the 290th to 334th amino acid residues of the polypeptide set forth in SEQ ID NO: 1;

A represents an 8-mer repeat sequence contained in a 47-kd region of a SERA polypeptide of *Plasmodium falciparum*;

B represents the amino acid sequence set forth in SEQ ID NO: 9;

Y represents any one selected from A-A, A-B, and B; and n represents an integer of 0 or 1.

2. The polypeptide according to claim 1, wherein, in formula (1), Y is A-B or B.

3. The polypeptide according to claim 1, wherein, in formula (1), A is an amino acid sequence selected from SEQ ID NOS: 2 to 8.

4. The polypeptide according to claim 1, comprising the amino acid sequence set forth in one of SEQ ID NOS: 10 to 14.

5. A polynucleotide encoding the polypeptides of any one of claims 1 to 4.

* * * * *

SEQUENCE LISTING

```
<160> NUMBER OF SEQ ID NOS: 37

<210> SEQ ID NO 1
<211> LENGTH: 334
<212> TYPE: PRT
<213> ORGANISM: artificial sequence
<220> FEATURE:
<223> OTHER INFORMATION: Synthetic Construct; an amino acid sequence of
      polypeptide (2).

<400> SEQUENCE: 1

Met Lys Asn Val Ile Lys Cys Thr Gly Glu Ser Gln Thr Gly Asn Thr
1               5                   10                  15

Gly Gly Gly Gln Ala Gly Asn Thr Val Gly Asp Gln Ala Gly Ser Thr
            20                  25                  30
```

```
Gly Gly Ser Pro Gln Gly Ser Thr Gly Ala Ser Gln Pro Gly Ser Ser
        35                  40                  45

Glu Pro Ser Asn Pro Val Ser Ser Gly His Ser Val Ser Thr Val Ser
 50                  55                  60

Val Ser Gln Thr Ser Thr Ser Ser Glu Lys Gln Asp Thr Ile Gln Val
 65                  70                  75                  80

Lys Ser Ala Leu Leu Lys Asp Tyr Met Gly Leu Lys Val Thr Gly Pro
                 85                  90                  95

Cys Asn Glu Asn Phe Ile Met Phe Leu Val Pro His Ile Tyr Ile Asp
                100                 105                 110

Val Asp Thr Glu Asp Thr Asn Ile Glu Leu Arg Thr Thr Leu Lys Glu
                115                 120                 125

Thr Asn Asn Ala Ile Ser Phe Glu Ser Asn Ser Gly Ser Leu Glu Lys
130                 135                 140

Lys Lys Tyr Val Lys Leu Pro Ser Asn Gly Thr Thr Gly Glu Gln Gly
145                 150                 155                 160

Ser Ser Thr Gly Thr Val Arg Gly Asp Thr Glu Pro Ile Ser Asp Ser
                165                 170                 175

Ser Glu Ser Leu Pro Ala Asn Gly Pro Asp Ser Pro Thr Val Lys Pro
                180                 185                 190

Pro Arg Asn Leu Gln Asn Ile Cys Glu Thr Gly Lys Asn Phe Lys Leu
                195                 200                 205

Val Val Tyr Ile Lys Glu Asn Thr Leu Ile Ile Lys Trp Lys Val Tyr
                210                 215                 220

Gly Glu Thr Lys Asp Thr Thr Glu Asn Asn Lys Val Asp Val Arg Lys
225                 230                 235                 240

Tyr Leu Ile Asn Glu Lys Glu Thr Pro Phe Thr Ser Ile Leu Ile His
                245                 250                 255

Ala Tyr Lys Glu His Asn Gly Thr Asn Leu Ile Glu Ser Lys Asn Tyr
                260                 265                 270

Ala Leu Gly Ser Asp Ile Pro Glu Lys Cys Asp Thr Leu Ala Ser Asn
                275                 280                 285

Cys Phe Leu Ser Gly Asn Phe Asn Ile Glu Lys Cys Phe Gln Cys Ala
                290                 295                 300

Leu Leu Val Glu Lys Glu Asn Lys Asn Asp Val Cys Tyr Lys Tyr Leu
305                 310                 315                 320

Ser Glu Asp Ile Val Ser Asn Phe Lys Glu Ile Lys Ala Glu
                325                 330

<210> SEQ ID NO 2
<211> LENGTH: 40
<212> TYPE: PRT
<213> ORGANISM: artificial sequence
<220> FEATURE:
<223> OTHER INFORMATION: Synthetic Construct; an amino acid sequence of
      A1.

<400> SEQUENCE: 2

Thr Gly Glu Ser Gln Thr Gly Asn Thr Gly Gly Gly Gln Ala Gly Asn
1               5                   10                  15

Thr Val Gly Asp Gln Ala Gly Ser Thr Gly Gly Ser Pro Gln Gly Ser
                20                  25                  30

Thr Gly Ala Ser Gln Pro Gly Ser
                35                  40
```

```
<210> SEQ ID NO 3
<211> LENGTH: 56
<212> TYPE: PRT
<213> ORGANISM: artificial sequence
<220> FEATURE:
<223> OTHER INFORMATION: Synthetic Construct; an amino acid sequence of
      A2.

<400> SEQUENCE: 3

Thr Gly Glu Ser Gln Thr Gly Asn Thr Gly Gly Gln Ala Gly Asn
1               5                   10                  15

Thr Gly Gly Asp Gln Ala Gly Ser Thr Gly Gly Ser Pro Gln Gly Ser
            20                  25                  30

Thr Gly Ala Ser Pro Gln Gly Ser Thr Gly Ala Ser Pro Gln Gly Ser
        35                  40                  45

Thr Gly Ala Ser Gln Pro Gly Ser
    50                  55

<210> SEQ ID NO 4
<211> LENGTH: 48
<212> TYPE: PRT
<213> ORGANISM: artificial sequence
<220> FEATURE:
<223> OTHER INFORMATION: Synthetic Construct; an amino acid sequence of
      A3.

<400> SEQUENCE: 4

Thr Gly Glu Ser Gln Thr Gly Asn Thr Gly Gly Gln Ala Gly Asn
1               5                   10                  15

Thr Val Gly Asp Gln Ala Gly Asn Thr Val Gly Asp Gln Ala Gly Ser
            20                  25                  30

Thr Gly Gly Ser Pro Gln Gly Ser Thr Gly Ala Ser Gln Pro Gly Ser
        35                  40                  45

<210> SEQ ID NO 5
<211> LENGTH: 48
<212> TYPE: PRT
<213> ORGANISM: artificial sequence
<220> FEATURE:
<223> OTHER INFORMATION: Synthetic Construct; an amino acid sequence of
      A4.

<400> SEQUENCE: 5

Thr Gly Glu Ser Gln Thr Gly Asn Thr Gly Gly Gln Ala Gly Asn
1               5                   10                  15

Thr Gly Gly Gly Gln Ala Gly Asn Thr Val Gly Asp Gln Ala Gly Ser
            20                  25                  30

Thr Gly Gly Ser Pro Gln Gly Ser Thr Gly Ala Ser Gln Pro Gly Ser
        35                  40                  45

<210> SEQ ID NO 6
<211> LENGTH: 48
<212> TYPE: PRT
<213> ORGANISM: artificial sequence
<220> FEATURE:
<223> OTHER INFORMATION: Synthetic Construct; an amino acid sequence of
      A5.

<400> SEQUENCE: 6

Thr Gly Glu Ser Gln Thr Gly Asn Thr Gly Gly Gln Val Gly Asn
1               5                   10                  15

Thr Gly Gly Gly Gln Ala Gly Ser Thr Gly Gly Ser Pro Gln Gly Ser
            20                  25                  30
```

-continued

Thr Gly Ala Ser Gln Pro Gly Ser Ser Glu Pro Ser Asn Pro Val Ser
            35                  40                  45

<210> SEQ ID NO 7
<211> LENGTH: 48
<212> TYPE: PRT
<213> ORGANISM: artificial sequence
<220> FEATURE:
<223> OTHER INFORMATION: Synthetic Construct; an amino acid sequence of
      A6.

<400> SEQUENCE: 7

Thr Gly Glu Ser Gln Thr Gly Asn Thr Gly Gly Gln Ala Gly Asn
1               5                   10                  15

Thr Val Gly Gly Gln Ala Gly Asn Thr Gly Gly Gln Ala Gly Asn
            20                  25                  30

Thr Gly Gly Asp Pro Gln Gly Ser Thr Gly Gly Ser Gln Pro Gly Ser
            35                  40                  45

<210> SEQ ID NO 8
<211> LENGTH: 56
<212> TYPE: PRT
<213> ORGANISM: artificial sequence
<220> FEATURE:
<223> OTHER INFORMATION: Synthetic Construct; an amino acid sequence of
      A7.

<400> SEQUENCE: 8

Thr Gly Glu Ser Gln Thr Gly Asn Ala Gly Gly Gln Ala Gly Asn
1               5                   10                  15

Thr Val Gly Asp Gln Ala Gly Ser Thr Gly Gly Ser Pro Gln Gly Ser
            20                  25                  30

Thr Gly Ala Ser Pro Gln Gly Ser Thr Gly Ala Ser Pro Gln Gly Ser
            35                  40                  45

Thr Gly Ala Ser Gln Pro Gly Ser
         50                  55

<210> SEQ ID NO 9
<211> LENGTH: 25
<212> TYPE: PRT
<213> ORGANISM: artificial sequence
<220> FEATURE:
<223> OTHER INFORMATION: Synthetic Construct; an amino acid sequence of
      B.

<400> SEQUENCE: 9

Ser Glu Pro Ser Asn Pro Val Ser Ser Gly His Ser Val Ser Thr Val
1               5                   10                  15

Ser Val Ser Gln Thr Ser Thr Ser Ser
            20                  25

<210> SEQ ID NO 10
<211> LENGTH: 418
<212> TYPE: PRT
<213> ORGANISM: artificial sequence
<220> FEATURE:
<223> OTHER INFORMATION: Synthetic Construct; an amino acid sequence of
      SE36-1.

<400> SEQUENCE: 10

Met Lys Asn Val Ile Lys Cys Thr Gly Glu Ser Gln Thr Gly Asn Thr
1               5                   10                  15

Gly Gly Gly Gln Ala Gly Asn Thr Val Gly Asp Gln Ala Gly Ser Thr
            20                  25                  30

Gly Gly Ser Pro Gln Gly Ser Thr Gly Ala Ser Gln Pro Gly Ser Ser
            35                  40                  45

Glu Pro Ser Asn Pro Val Ser Ser Gly His Ser Val Ser Thr Val Ser
 50                  55                  60

Val Ser Gln Thr Ser Thr Ser Ser Glu Lys Gln Asp Thr Ile Gln Val
 65                  70                  75                  80

Lys Ser Ala Leu Leu Lys Asp Tyr Met Gly Leu Lys Val Thr Gly Pro
                 85                  90                  95

Cys Asn Glu Asn Phe Ile Met Phe Leu Val Pro His Ile Tyr Ile Asp
                100                 105                 110

Val Asp Thr Glu Asp Thr Asn Ile Glu Leu Arg Thr Thr Leu Lys Glu
                115                 120                 125

Thr Asn Asn Ala Ile Ser Phe Glu Ser Asn Ser Gly Ser Leu Glu Lys
            130                 135                 140

Lys Lys Tyr Val Lys Leu Pro Ser Asn Gly Thr Thr Gly Glu Gln Gly
145                 150                 155                 160

Ser Ser Thr Gly Thr Val Arg Gly Asp Thr Glu Pro Ile Ser Asp Ser
                165                 170                 175

Ser Thr Gly Glu Ser Gln Thr Gly Asn Thr Gly Gly Gln Ala Gly
            180                 185                 190

Asn Thr Gly Gly Asp Gln Ala Gly Ser Thr Gly Gly Ser Pro Gln Gly
                195                 200                 205

Ser Thr Gly Ala Ser Pro Gln Gly Ser Thr Gly Ala Ser Pro Gln Gly
            210                 215                 220

Ser Thr Gly Ala Ser Gln Pro Gly Ser Ser Glu Pro Ser Asn Pro Val
225                 230                 235                 240

Ser Ser Gly His Ser Val Ser Thr Val Ser Val Ser Gln Thr Ser Thr
                245                 250                 255

Ser Ser Asp Ser Ser Glu Ser Leu Pro Ala Asn Gly Pro Asp Ser Pro
            260                 265                 270

Thr Val Lys Pro Pro Arg Asn Leu Gln Asn Ile Cys Glu Thr Gly Lys
                275                 280                 285

Asn Phe Lys Leu Val Val Tyr Ile Lys Glu Asn Thr Leu Ile Ile Lys
            290                 295                 300

Trp Lys Val Tyr Gly Glu Thr Lys Asp Thr Thr Glu Asn Asn Lys Val
305                 310                 315                 320

Asp Val Arg Lys Tyr Leu Ile Asn Glu Lys Glu Thr Pro Phe Thr Ser
                325                 330                 335

Ile Leu Ile His Ala Tyr Lys Glu His Asn Gly Thr Asn Leu Ile Glu
            340                 345                 350

Ser Lys Asn Tyr Ala Leu Gly Ser Asp Ile Pro Glu Lys Cys Asp Thr
            355                 360                 365

Leu Ala Ser Asn Cys Phe Leu Ser Gly Asn Phe Asn Ile Glu Lys Cys
 370                 375                 380

Phe Gln Cys Ala Leu Leu Val Glu Lys Glu Asn Lys Asn Asp Val Cys
385                 390                 395                 400

Tyr Lys Tyr Leu Ser Glu Asp Ile Val Ser Asn Phe Lys Glu Ile Lys
                405                 410                 415

Ala Glu

<210> SEQ ID NO 11
<211> LENGTH: 494
<212> TYPE: PRT

<213> ORGANISM: artificial sequence
<220> FEATURE:
<223> OTHER INFORMATION: Synthetic Construct; an amino acid sequence of SE36-2.

<400> SEQUENCE: 11

```
Met Lys Asn Val Ile Lys Cys Thr Gly Glu Ser Gln Thr Gly Asn Thr
1               5                   10                  15

Gly Gly Gly Gln Ala Gly Asn Thr Val Gly Asp Gln Ala Gly Ser Thr
            20                  25                  30

Gly Gly Ser Pro Gln Gly Ser Thr Gly Ala Ser Gln Pro Gly Ser Ser
        35                  40                  45

Glu Pro Ser Asn Pro Val Ser Ser Gly His Ser Val Ser Thr Val Ser
50                  55                  60

Val Ser Gln Thr Ser Thr Ser Ser Glu Lys Gln Asp Thr Ile Gln Val
65                  70                  75                  80

Lys Ser Ala Leu Leu Lys Asp Tyr Met Gly Leu Lys Val Thr Gly Pro
                85                  90                  95

Cys Asn Glu Asn Phe Ile Met Phe Leu Val Pro His Ile Tyr Ile Asp
            100                 105                 110

Val Asp Thr Glu Asp Thr Asn Ile Glu Leu Arg Thr Thr Leu Lys Glu
        115                 120                 125

Thr Asn Asn Ala Ile Ser Phe Glu Ser Asn Ser Gly Ser Leu Glu Lys
130                 135                 140

Lys Lys Tyr Val Lys Leu Pro Ser Asn Gly Thr Thr Gly Glu Gln Gly
145                 150                 155                 160

Ser Ser Thr Gly Thr Val Arg Gly Asp Thr Glu Pro Ile Ser Asp Ser
                165                 170                 175

Ser Thr Gly Glu Ser Gln Thr Gly Asn Thr Gly Gly Gly Gln Ala Gly
            180                 185                 190

Asn Thr Gly Gly Asp Gln Ala Gly Ser Thr Gly Gly Ser Pro Gln Gly
        195                 200                 205

Ser Thr Gly Ala Ser Pro Gln Gly Ser Thr Gly Ala Ser Pro Gln Gly
210                 215                 220

Ser Thr Gly Ala Ser Gln Pro Gly Ser Ser Glu Pro Ser Asn Pro Val
225                 230                 235                 240

Ser Ser Gly His Ser Val Ser Thr Val Ser Val Ser Gln Thr Ser Thr
                245                 250                 255

Ser Ser Asp Ser Ser Glu Ser Leu Pro Ala Asn Gly Pro Asp Ser Pro
            260                 265                 270

Thr Val Lys Pro Pro Arg Asn Leu Gln Asn Ile Cys Glu Thr Gly Lys
        275                 280                 285

Asn Phe Lys Leu Val Val Tyr Ile Lys Glu Asn Thr Leu Ile Ile Lys
290                 295                 300

Trp Lys Val Tyr Gly Glu Thr Lys Asp Thr Thr Glu Asn Asn Lys Val
305                 310                 315                 320

Asp Val Arg Lys Tyr Leu Ile Asn Glu Lys Glu Thr Pro Phe Thr Ser
                325                 330                 335

Ile Leu Ile His Ala Tyr Thr Gly Glu Ser Gln Thr Gly Asn Thr Gly
            340                 345                 350

Gly Gly Gln Ala Gly Asn Thr Val Gly Asp Gln Ala Gly Asn Thr Val
        355                 360                 365

Gly Asp Gln Ala Gly Ser Thr Gly Gly Ser Pro Gln Gly Ser Thr Gly
370                 375                 380
```

```
Ala Ser Gln Pro Gly Ser Glu Pro Ser Asn Pro Val Ser Ser Gly
385                 390                 395                 400

His Ser Val Ser Thr Val Ser Val Ser Gln Thr Ser Thr Ser Ser His
                405                 410                 415

Ala Tyr Lys Glu His Asn Gly Thr Asn Leu Ile Glu Ser Lys Asn Tyr
            420                 425                 430

Ala Leu Gly Ser Asp Ile Pro Glu Lys Cys Asp Thr Leu Ala Ser Asn
        435                 440                 445

Cys Phe Leu Ser Gly Asn Phe Asn Ile Glu Lys Cys Phe Gln Cys Ala
    450                 455                 460

Leu Leu Val Glu Lys Glu Asn Lys Asn Asp Val Cys Tyr Lys Tyr Leu
465                 470                 475                 480

Ser Glu Asp Ile Val Ser Asn Phe Lys Glu Ile Lys Ala Glu
                485                 490

<210> SEQ ID NO 12
<211> LENGTH: 570
<212> TYPE: PRT
<213> ORGANISM: artificial sequence
<220> FEATURE:
<223> OTHER INFORMATION: Synthetic Construct; an amino acid sequence of
      SE36-3.

<400> SEQUENCE: 12

Met Lys Asn Val Ile Lys Cys Thr Gly Glu Ser Gln Thr Gly Asn Thr
1               5                   10                  15

Gly Gly Gly Gln Ala Gly Asn Thr Val Gly Asp Gln Ala Gly Ser Thr
            20                  25                  30

Gly Gly Ser Pro Gln Gly Ser Thr Gly Ala Ser Gln Pro Gly Ser Ser
        35                  40                  45

Glu Pro Ser Asn Pro Val Ser Ser Gly His Ser Val Ser Thr Val Ser
    50                  55                  60

Val Ser Gln Thr Ser Thr Ser Ser Glu Lys Gln Asp Thr Ile Gln Val
65                  70                  75                  80

Lys Ser Ala Leu Leu Lys Asp Tyr Met Gly Leu Lys Val Thr Gly Pro
                85                  90                  95

Cys Asn Glu Asn Phe Ile Met Phe Leu Val Pro His Ile Tyr Ile Asp
            100                 105                 110

Val Asp Thr Glu Asp Thr Asn Ile Glu Leu Arg Thr Thr Leu Lys Glu
        115                 120                 125

Thr Asn Asn Ala Ile Ser Phe Glu Ser Asn Ser Gly Ser Leu Glu Lys
    130                 135                 140

Lys Lys Tyr Val Lys Leu Pro Ser Asn Gly Thr Thr Gly Glu Gln Gly
145                 150                 155                 160

Ser Ser Thr Gly Thr Val Arg Gly Asp Thr Glu Pro Ile Ser Asp Ser
                165                 170                 175

Ser Thr Gly Glu Ser Gln Thr Gly Asn Thr Gly Gly Gln Ala Gly
            180                 185                 190

Asn Thr Gly Gly Asp Gln Ala Gly Ser Thr Gly Gly Ser Pro Gln Gly
        195                 200                 205

Ser Thr Gly Ala Ser Pro Gln Gly Ser Thr Gly Ala Ser Pro Gln Gly
    210                 215                 220

Ser Thr Gly Ala Ser Gln Pro Gly Ser Ser Glu Pro Ser Asn Pro Val
225                 230                 235                 240

Ser Ser Gly His Ser Val Ser Thr Val Ser Val Ser Gln Thr Ser Thr
                245                 250                 255
```

```
Ser Ser Asp Ser Ser Glu Ser Leu Pro Ala Asn Gly Pro Asp Ser Pro
                260                 265                 270

Thr Val Lys Pro Pro Arg Asn Leu Gln Asn Ile Cys Glu Thr Gly Lys
            275                 280                 285

Asn Phe Lys Leu Val Val Tyr Ile Lys Glu Asn Thr Leu Ile Ile Lys
290                 295                 300

Trp Lys Val Tyr Gly Glu Thr Lys Asp Thr Thr Glu Asn Asn Lys Val
305                 310                 315                 320

Asp Val Arg Lys Tyr Leu Ile Asn Glu Lys Glu Thr Pro Phe Thr Ser
                325                 330                 335

Ile Leu Ile His Ala Tyr Thr Gly Glu Ser Gln Thr Gly Asn Thr Gly
            340                 345                 350

Gly Gly Gln Ala Gly Asn Thr Val Gly Asp Gln Ala Gly Asn Thr Val
        355                 360                 365

Gly Asp Gln Ala Gly Ser Thr Gly Gly Ser Pro Gln Gly Ser Thr Gly
    370                 375                 380

Ala Ser Gln Pro Gly Ser Ser Glu Pro Ser Asn Pro Val Ser Ser Gly
385                 390                 395                 400

His Ser Val Ser Thr Val Ser Val Ser Gln Thr Ser Thr Ser Ser His
                405                 410                 415

Ala Tyr Lys Glu His Asn Gly Thr Asn Leu Ile Glu Ser Lys Asn Tyr
            420                 425                 430

Ala Leu Gly Ser Asp Ile Pro Glu Lys Cys Asp Thr Leu Ala Ser Asn
        435                 440                 445

Cys Thr Gly Glu Ser Gln Thr Gly Asn Thr Gly Gly Gln Ala Gly
    450                 455                 460

Asn Thr Gly Gly Gly Gln Ala Gly Asn Thr Val Gly Asp Gln Ala Gly
465                 470                 475                 480

Ser Thr Gly Gly Ser Pro Gln Gly Ser Thr Gly Ala Ser Gln Pro Gly
                485                 490                 495

Ser Ser Glu Pro Ser Asn Pro Val Ser Ser Gly His Ser Val Ser Thr
            500                 505                 510

Val Ser Val Ser Gln Thr Ser Thr Ser Ser Asn Cys Phe Leu Ser
        515                 520                 525

Gly Asn Phe Asn Ile Glu Lys Cys Phe Gln Cys Ala Leu Leu Val Glu
    530                 535                 540

Lys Glu Asn Lys Asn Asp Val Cys Tyr Lys Tyr Leu Ser Glu Asp Ile
545                 550                 555                 560

Val Ser Asn Phe Lys Glu Ile Lys Ala Glu
                565                 570

<210> SEQ ID NO 13
<211> LENGTH: 653
<212> TYPE: PRT
<213> ORGANISM: artificial sequence
<220> FEATURE:
<223> OTHER INFORMATION: Synthetic Construct; an amino acid sequence of
      SE36-4.

<400> SEQUENCE: 13

Met Lys Asn Val Ile Lys Cys Thr Gly Glu Ser Gln Thr Gly Asn Thr
1               5                   10                  15

Gly Gly Gly Gln Ala Gly Asn Thr Val Gly Asp Gln Ala Gly Ser Thr
            20                  25                  30

Gly Gly Ser Pro Gln Gly Ser Thr Gly Ala Ser Gln Pro Gly Ser Ser
```

```
            35                  40                  45
Glu Pro Ser Asn Pro Val Ser Ser Gly His Ser Val Ser Thr Val Ser
 50                  55                  60

Val Ser Gln Thr Ser Thr Ser Ser Glu Lys Gln Asp Thr Ile Gln Val
 65                  70                  75                  80

Lys Ser Ala Leu Leu Lys Asp Tyr Met Gly Leu Lys Val Thr Gly Pro
                 85                  90                  95

Cys Asn Glu Asn Phe Ile Met Phe Leu Val Pro His Ile Tyr Ile Asp
            100                 105                 110

Val Asp Thr Glu Asp Thr Asn Ile Glu Leu Arg Thr Thr Leu Lys Glu
            115                 120                 125

Thr Asn Asn Ala Ile Ser Phe Glu Ser Asn Ser Gly Ser Leu Glu Lys
            130                 135                 140

Lys Lys Tyr Val Lys Leu Pro Ser Asn Gly Thr Thr Gly Glu Gln Gly
145                 150                 155                 160

Ser Ser Thr Gly Thr Val Arg Gly Asp Thr Glu Pro Ile Ser Asp Ser
                165                 170                 175

Ser Thr Gly Glu Ser Gln Thr Gly Asn Thr Gly Gly Gln Ala Gly
                180                 185                 190

Asn Thr Gly Gly Asp Gln Ala Gly Ser Thr Gly Gly Ser Pro Gln Gly
                195                 200                 205

Ser Thr Gly Ala Ser Pro Gln Gly Ser Thr Gly Ala Ser Pro Gln Gly
                210                 215                 220

Ser Thr Gly Ala Ser Gln Pro Gly Ser Gly Ser Thr Gly Glu Ser Gln
225                 230                 235                 240

Thr Gly Asn Thr Gly Gly Gln Val Gly Asn Thr Gly Gly Gln
                245                 250                 255

Ala Gly Ser Thr Gly Gly Ser Pro Gln Gly Ser Thr Gly Ala Ser Gln
                260                 265                 270

Pro Gly Ser Ser Glu Pro Ser Asn Pro Val Ser Asp Ser Ser Glu Ser
                275                 280                 285

Leu Pro Ala Asn Gly Pro Asp Ser Pro Thr Val Lys Pro Pro Arg Asn
290                 295                 300

Leu Gln Asn Ile Cys Glu Thr Gly Lys Asn Phe Lys Leu Val Val Tyr
305                 310                 315                 320

Ile Lys Glu Asn Thr Leu Ile Ile Lys Trp Lys Val Tyr Gly Glu Thr
                325                 330                 335

Lys Asp Thr Thr Glu Asn Asn Lys Val Asp Val Arg Lys Tyr Leu Ile
                340                 345                 350

Asn Glu Lys Glu Thr Pro Phe Thr Ser Ile Leu Ile His Ala Tyr Thr
                355                 360                 365

Gly Glu Ser Gln Thr Gly Asn Thr Gly Gly Gln Ala Gly Asn Thr
                370                 375                 380

Val Gly Asp Gln Ala Gly Asn Thr Val Gly Asp Gln Ala Gly Ser Thr
385                 390                 395                 400

Gly Gly Ser Pro Gln Gly Ser Thr Gly Ala Ser Gln Pro Gly Ser Leu
                405                 410                 415

Lys Thr Gly Glu Ser Gln Thr Gly Asn Thr Gly Gly Gln Ala Gly
                420                 425                 430

Asn Thr Val Gly Gly Gln Ala Gly Asn Thr Gly Gly Gln Ala Gly
                435                 440                 445

Asn Thr Gly Gly Asp Pro Gln Gly Ser Thr Gly Gly Ser Gln Pro Gly
                450                 455                 460
```

```
Ser His Ala Tyr Lys Glu His Asn Gly Thr Asn Leu Ile Glu Ser Lys
465                 470                 475                 480

Asn Tyr Ala Leu Gly Ser Asp Ile Pro Glu Lys Cys Asp Thr Leu Ala
            485                 490                 495

Ser Asn Cys Thr Gly Glu Ser Gln Thr Gly Asn Thr Gly Gly Gly Gln
        500                 505                 510

Ala Gly Asn Thr Gly Gly Gly Gln Ala Gly Asn Thr Val Gly Asp Gln
    515                 520                 525

Ala Gly Ser Thr Gly Gly Ser Pro Gln Gly Ser Thr Gly Ala Ser Gln
530                 535                 540

Pro Gly Ser Leu Glu Thr Gly Glu Ser Gln Thr Gly Asn Ala Gly Gly
545                 550                 555                 560

Gly Gln Ala Gly Asn Thr Val Gly Asp Gln Ala Gly Ser Thr Gly Gly
            565                 570                 575

Ser Pro Gln Gly Ser Thr Gly Ala Ser Gln Pro Gly Ser Thr Gly Ala
        580                 585                 590

Ser Pro Gln Gly Ser Thr Gly Ala Ser Gln Pro Gly Ser Ser Asn Cys
    595                 600                 605

Phe Leu Ser Gly Asn Phe Asn Ile Glu Lys Cys Phe Gln Cys Ala Leu
610                 615                 620

Leu Val Glu Lys Glu Asn Lys Asn Asp Val Cys Tyr Lys Tyr Leu Ser
625                 630                 635                 640

Glu Asp Ile Val Ser Asn Phe Lys Glu Ile Lys Ala Glu
            645                 650

<210> SEQ ID NO 14
<211> LENGTH: 418
<212> TYPE: PRT
<213> ORGANISM: artificial sequence
<220> FEATURE:
<223> OTHER INFORMATION: Synthetic Construct; an amino acid sequence of
      SE36-5.

<400> SEQUENCE: 14

Met Lys Asn Val Ile Lys Cys Thr Gly Glu Ser Gln Thr Gly Asn Thr
1               5                   10                  15

Gly Gly Gly Gln Ala Gly Asn Thr Val Gly Asp Gln Ala Gly Ser Thr
            20                  25                  30

Gly Gly Ser Pro Gln Gly Ser Thr Gly Ala Ser Gln Pro Gly Ser Ser
        35                  40                  45

Glu Pro Ser Asn Pro Val Ser Ser Gly His Ser Val Ser Thr Val Ser
    50                  55                  60

Val Ser Gln Thr Ser Thr Ser Ser Glu Lys Gln Asp Thr Ile Gln Val
65                  70                  75                  80

Lys Ser Ala Leu Leu Lys Asp Tyr Met Gly Leu Lys Val Thr Gly Pro
                85                  90                  95

Cys Asn Glu Asn Phe Ile Met Phe Leu Val Pro His Ile Tyr Ile Asp
            100                 105                 110

Val Asp Thr Glu Asp Thr Asn Ile Glu Leu Arg Thr Leu Lys Glu
        115                 120                 125

Thr Asn Asn Ala Ile Ser Phe Glu Ser Asn Ser Gly Ser Leu Glu Lys
    130                 135                 140

Lys Lys Tyr Val Lys Leu Pro Ser Asn Gly Thr Thr Gly Glu Gln Gly
145                 150                 155                 160

Ser Ser Thr Gly Thr Val Arg Gly Asp Thr Glu Pro Ile Ser Asp Ser
```

```
                            165                 170                 175
        Ser Ser Glu Pro Ser Asn Pro Val Ser Ser Gly His Ser Val Ser Thr
                        180                 185                 190

Val Ser Val Ser Gln Thr Ser Thr Ser Ser Asp Ser Ser Glu Ser Leu
                    195                 200                 205

Pro Ala Asn Gly Pro Asp Ser Pro Thr Val Lys Pro Pro Arg Asn Leu
                210                 215                 220

Gln Asn Ile Cys Glu Thr Gly Lys Asn Phe Lys Leu Val Val Tyr Ile
        225                 230                 235                 240

Lys Glu Asn Thr Leu Ile Ile Lys Trp Lys Val Tyr Gly Glu Thr Lys
                        245                 250                 255

Asp Thr Thr Glu Asn Asn Lys Val Asp Val Arg Lys Tyr Leu Ile Asn
                    260                 265                 270

Glu Lys Glu Thr Pro Phe Thr Ser Ile Leu Ile His Ala Tyr Ser Glu
                275                 280                 285

Pro Ser Asn Pro Val Ser Ser Gly His Ser Val Ser Thr Val Ser Val
            290                 295                 300

Ser Gln Thr Ser Thr Ser Ser His Ala Tyr Lys Glu His Asn Gly Thr
        305                 310                 315                 320

Asn Leu Ile Glu Ser Lys Asn Tyr Ala Leu Gly Ser Asp Ile Pro Glu
                        325                 330                 335

Lys Cys Asp Thr Leu Ala Ser Asn Cys Ser Glu Pro Ser Asn Pro Val
                    340                 345                 350

Ser Ser Gly His Ser Val Ser Thr Val Ser Val Ser Gln Thr Ser Thr
                355                 360                 365

Ser Ser Ser Asn Cys Phe Leu Ser Gly Asn Phe Asn Ile Glu Lys Cys
        370                 375                 380

Phe Gln Cys Ala Leu Leu Val Glu Lys Glu Asn Lys Asn Asp Val Cys
        385                 390                 395                 400

Tyr Lys Tyr Leu Ser Glu Asp Ile Val Ser Asn Phe Lys Glu Ile Lys
                        405                 410                 415

Ala Glu

<210> SEQ ID NO 15
<211> LENGTH: 264
<212> TYPE: PRT
<213> ORGANISM: artificial sequence
<220> FEATURE:
<223> OTHER INFORMATION: Synthetic Construct; an amino acid sequence of
      negative SE36.

<400> SEQUENCE: 15

Met Ser Glu Lys Gln Asp Thr Ile Gln Val Lys Ser Ala Leu Leu Lys
        1               5                  10                  15

Asp Tyr Met Gly Leu Lys Val Thr Gly Pro Cys Asn Glu Asn Phe Ile
                        20                  25                  30

Met Phe Leu Val Pro His Ile Tyr Ile Asp Val Asp Thr Glu Asp Thr
                    35                  40                  45

Asn Ile Glu Leu Arg Thr Thr Leu Lys Glu Thr Asn Asn Ala Ile Ser
                50                  55                  60

Phe Glu Ser Asn Ser Gly Ser Leu Glu Lys Lys Tyr Val Lys Leu
        65                  70                  75                  80

Pro Ser Asn Gly Thr Thr Gly Glu Gln Gly Ser Ser Thr Gly Thr Val
                        85                  90                  95

Arg Gly Asp Thr Glu Pro Ile Ser Asp Ser Ser Glu Ser Leu Pro Ala
```

```
            100                 105                 110
Asn Gly Pro Asp Ser Pro Thr Val Lys Pro Pro Arg Asn Leu Gln Asn
        115                 120                 125

Ile Cys Glu Thr Gly Lys Asn Phe Lys Leu Val Val Tyr Ile Lys Glu
        130                 135                 140

Asn Thr Leu Ile Ile Lys Trp Lys Val Tyr Gly Glu Thr Lys Asp Thr
145                 150                 155                 160

Thr Glu Asn Asn Lys Val Asp Val Arg Lys Tyr Leu Ile Asn Glu Lys
                165                 170                 175

Glu Thr Pro Phe Thr Ser Ile Leu Ile His Ala Tyr Lys Glu His Asn
            180                 185                 190

Gly Thr Asn Leu Ile Glu Ser Lys Asn Tyr Ala Leu Gly Ser Asp Ile
        195                 200                 205

Pro Glu Lys Cys Asp Thr Leu Ala Ser Asn Cys Phe Leu Ser Gly Asn
        210                 215                 220

Phe Asn Ile Glu Lys Cys Phe Gln Cys Ala Leu Leu Val Glu Lys Glu
225                 230                 235                 240

Asn Lys Asn Asp Val Cys Tyr Lys Tyr Leu Ser Glu Asp Ile Val Ser
                245                 250                 255

Asn Phe Lys Glu Ile Lys Ala Glu
            260
```

```
<210> SEQ ID NO 16
<211> LENGTH: 1005
<212> TYPE: DNA
<213> ORGANISM: artificial sequence
<220> FEATURE:
<223> OTHER INFORMATION: Synthetic Construct; a nucleotide sequence
      coding polypeptide (2).

<400> SEQUENCE: 16
atgaaaaacg tgatcaaatg taccggtgaa agccagaccg gtaataccgg cggtggtcag      60
gcaggcaaca cggttggcga ccaggcgggc tctaccggcg gctctccgca gggtagcaca     120
ggcgccagtc aacccggctc tagcgaaccg tctaacccag tgtcttctgg ccattctgtt     180
agtaccgtta gcgttagcca gaccagcacc tcttctgaaa acaagatac cattcaggtg     240 aaatctgcgc tgctgaaaga ttatatgggt ttaaaagtta cgggcccgtg taacgaaaat     300
ttcatcatgt tcctggttcc gcatatttat attgatgtgg ataccgaaga taccaatata     360
gagctccgta ccaccctgaa agaaaccaac aacgcgatct catttgaatc aaacagtggt     420
tcactggaaa aaaaaaata tgtgaagctt ccgtcaaacg gcaccaccgg tgaacagggt     480
tcaagtacag gcaccgttcg cggcgatacc gaaccgattt cagactcgag tgaaagtctt     540
ccggcgaatg gccggattc cccgaccgtt aaacccccgc gtaacctgca gaacatctgt     600
gaaaccggca aaaacttcaa actggtggtg tatattaagg agaatacatt aatcattaaa     660
tggaaagtgt acggcgaaac caagatacc accgaaaata caaagtgga cgtacgcaag     720 tatctgatta cgaaaagga acccgtttt actagtattc taatccatgc atataaagaa     780
cataatggca ccaacctgat cgaaagtaaa actacgcgc tgggctcaga cattccggaa     840
aaatgtgata ccctggcgtc caattgcttt ctgagtggta actttaacat gaaaaatgc     900 tttcagtgcg cgctgctggt ggaaaaagaa aataaaaacg acgtgtgtta caataccta     960 agcgaagata ttgtgtctaa tttcaaggag atcaaagcgg agtaa                   1005

<210> SEQ ID NO 17
```

```
<211> LENGTH: 1254
<212> TYPE: DNA
<213> ORGANISM: artificial seqeunce
<220> FEATURE:
<223> OTHER INFORMATION: Synthetic Construct; a nucleotide sequence
      coding SE36-1.

<400> SEQUENCE: 17
atgaaaaacg tgatcaaatg taccggtgaa agccagaccg gtaataccgg cggtggtcag     60
gcaggcaaca cggttggcga ccaggcgggc tctaccggcg gctctccgca gggtagcaca    120
ggcgccagtc aacccggctc tagcgaaccg tctaacccag tgtcttctgg ccattctgtt    180
agtaccgtta gcgttagcca gaccagcacc tcttctgaaa acaagatac cattcaggtg     240
aaatctgcgc tgctgaaaga ttatatgggt ttaaaagtta cgggcccgtg taacgaaaat    300
ttcatcatgt tcctggttcc gcatatttat attgatgtgg ataccgaaga taccaatata    360
gagctccgta ccaccctgaa agaaaccaac aacgcgatct catttgaatc aaacagtggt    420
tcactggaaa aaaaaaaata tgtgaagctt ccgtcaaacg gcaccaccgg tgaacagggt    480
tcaagtacag gcaccgttcg cggcgatacc gaaccgattt cagactcgag accggtgaat    540
ctcaaaccgg taacactggt ggcggtcagg caggtaacac cggcggagat caggcaggaa    600
gcaccggcgg cagcccgcaa ggaagcacag gcgcgagtcc gcagggtagc actggtgcga    660
gcccacaggg tagtacaggc gcaagtcaac ctggaagctc tgaaccgagt aacccggtta    720
gctctggaca tagtgttagt accgtttcgg tttctcagac gtctacgagt tcgctcgagt    780
gaaagtcttc cggcgaatgg cccggattcc ccgaccgtta aaccccgcg taacctgcag     840
aacatctgtg aaaccggcaa aaacttcaaa ctggtggtgt atattaagga gaatacatta    900
atcattaaat ggaaagtgta cggcgaaacc aaagatacca ccgaaaataa caaagtggac    960
gtacgcaagt atctgattaa cgaaaggaa accccgttta ctagtattct aatccatgca    1020
tataagaac ataatggcac caacctgatc gaaagtaaaa actacgcgct gggctcagac    1080
attccggaaa atgtgatac cctggcgtcc aattgctttc tgagtggtaa ctttaacatt    1140
gaaaaatgct ttcagtgcgc gctgctggtg aaaaagaaa ataaaaacga cgtgtgttac    1200
aaatacctaa gcgaagatat tgtgtctaat ttcaaggaga tcaaagcgga gtaa          1254

<210> SEQ ID NO 18
<211> LENGTH: 1482
<212> TYPE: DNA
<213> ORGANISM: artificial sequence
<220> FEATURE:
<223> OTHER INFORMATION: Synthetic Construct; a nucleotide sequence
      coding SE36-2.

<400> SEQUENCE: 18
atgaaaaacg tgatcaaatg taccggtgaa agccagaccg gtaataccgg cggtggtcag     60
gcaggcaaca cggttggcga ccaggcgggc tctaccggcg gctctccgca gggtagcaca    120
ggcgccagtc aacccggctc tagcgaaccg tctaacccag tgtcttctgg ccattctgtt    180
agtaccgtta gcgttagcca gaccagcacc tcttctgaaa acaagatac cattcaggtg     240
aaatctgcgc tgctgaaaga ttatatgggt ttaaaagtta cgggcccgtg taacgaaaat    300
ttcatcatgt tcctggttcc gcatatttat attgatgtgg ataccgaaga taccaatata    360
gagctccgta ccaccctgaa agaaaccaac aacgcgatct catttgaatc aaacagtggt    420
tcactggaaa aaaaaaaata tgtgaagctt ccgtcaaacg gcaccaccgg tgaacagggt    480
tcaagtacag gcaccgttcg cggcgatacc gaaccgattt cagactcgag accggtgaat    540
```

| | |
|---|---|
| ctcaaaccgg taacactggt ggcggtcagg caggtaacac cggcggagat caggcaggaa | 600 |
| gcaccggcgg cagcccgcaa ggaagcacag gcgcgagtcc gcagggtagc actggtgcga | 660 |
| gcccacaggg tagtacaggc gcaagtcaac ctggaagctc tgaaccgagt aacccggtta | 720 |
| gctctggaca tagtgttagt accgtttcgg tttctcagac gtctacgagt tcgctcgagt | 780 |
| gaaagtcttc cggcgaatgg cccggattcc ccgaccgtta aaccccgcg taacctgcag | 840 |
| aacatctgtg aaaccggcaa aaacttcaaa ctggtggtgt atattaagga gaatacatta | 900 |
| atcattaaat ggaaagtgta cggcgaaacc aaagatacca ccgaaaataa caaagtggac | 960 |
| gtacgcaagt atctgattaa cgaaaaggaa accccgttta ctagtattct aatccatgca | 1020 |
| tataccggcg aaagccaaac gggcaacaca ggtggtggtc aggccggtaa tactgtgggc | 1080 |
| gatcaagctg gtaacaccgt gggcgatcag gcgggctcta caggtggcag ccctcagggc | 1140 |
| agcaccggag catctcaacc tggtagtagc gagccgtcta atccagtgag ctctggtcat | 1200 |
| tccgttagca ccgtgagcgt gagtcagacg agcacgagct cgcatgcata taagaacat | 1260 |
| aatggcacca acctgatcga agtaaaaac tacgcgctgg gctcagacat tccggaaaaa | 1320 |
| tgtgataccc tggcgtccaa ttgctttctg agtggtaact ttaacattga aaatgctttt | 1380 |
| cagtgcgcgc tgctggtgga aaaagaaat aaaaacgacg tgtgttacaa atacctaagc | 1440 |
| gaagatattg tgtctaattt caaggagatc aaagcggagt aa | 1482 |

<210> SEQ ID NO 19
<211> LENGTH: 1713
<212> TYPE: DNA
<213> ORGANISM: artificial sequence
<220> FEATURE:
<223> OTHER INFORMATION: Synthetic Construct; a nucleotide sequence
      coding SE36-3.

<400> SEQUENCE: 19

| | |
|---|---|
| atgaaaaacg tgatcaaatg taccggtgaa agccagaccg gtaataccgg cggtggtcag | 60 |
| gcaggcaaca cggttggcga ccaggcgggc tctaccggcg gctctccgca gggtagcaca | 120 |
| ggcgccagtc aacccggctc tagcgaaccg tctaacccag tgtcttctgg ccattctgtt | 180 |
| agtaccgtta gcgttagcca gaccagcacc tcttctgaaa acaagatac cattcaggtg | 240 |
| aaatctgcgc tgctgaaaga ttatatgggt ttaaaagtta cgggcccgtg taacgaaaat | 300 |
| ttcatcatgt tcctggttcc gcatatttat attgatgtgg ataccgaaga taccaatata | 360 |
| gagctccgta ccaccctgaa agaaaccaac aacgcgatct catttgaatc aaacagtggt | 420 |
| tcactggaaa aaaaaaata tgtgaagctt ccgtcaaacg gcaccaccgg tgaacagggt | 480 |
| tcaagtacag gcaccgttcg cggcgatacc gaaccgattt cagactcgag taccggtgaa | 540 |
| tctcaaaccg gtaacactgg tggcggtcag gcaggtaaca ccggcggaga tcaggcagga | 600 |
| agcaccggcg gcagcccgca aggaagcaca ggcgcgagtc gcagggtag cactggtgcg | 660 |
| agcccacagg gtagtacagg cgcaagtcaa cctggaagct ctgaaccgag taacccggtt | 720 |
| agctctggac atagtgttag taccgtttcg gtttctcaga cgtctacgag ttcggactcg | 780 |
| agtgaaagtc ttccggcgaa tggcccggat tccccgaccg ttaaaccccc gcgtaacctg | 840 |
| cagaacatct gtgaaaccgg caaaaacttc aaactggtgg tgtatattaa ggagaataca | 900 |
| ttaatcatta aatggaaagt gtacggcgaa accaaagata ccaccgaaaa taacaaagtg | 960 |
| gacgtacgca agtatctgat taacgaaaag gaaaccccgt ttactagtat tctaatccat | 1020 |
| gcatataccg gcgaaagcca aacgggcaac acaggtggtg gtcaggccgg taatactgtg | 1080 |

```
ggcgatcaag ctggtaacac cgtgggcgat caggcgggct ctacaggtgg cagccctcag    1140
ggcagcaccg gagcatctca acctggtagt agcgagccgt ctaatccagt gagctctggt    1200
cattccgtta gcaccgtgag cgtgagtcag acgagcacga gctcgcatgc atataaagaa    1260
cataatggca ccaacctgat cgaaagtaaa aactacgcgc tgggctcaga cattccggaa    1320
aaatgtgata ccctggcgtc caattgcacc ggcgagagcc aaactggcaa cacgggtggt    1380
ggacaggctg gtaacactgg tggcggtcag gcaggcaata ctgttggtga tcaagctggt    1440
agtaccggcg gcagtccaca aggaagtact ggagcgagcc aaccgggctc tagcgaaccg    1500
agcaacccgg tgagcagtgg acatagcgtg agcaccgtta gcgttagtca gacctcgacc    1560
agcagttcca attgctttct gagtggtaac tttaacattg aaaaatgctt tcagtgcgcg    1620
ctgctggtgg aaaagaaaa taaaaacgac gtgtgttaca aatacctaag cgaagatatt    1680
gtgtctaatt tcaaggagat caaagcggag taa                                1713

<210> SEQ ID NO 20
<211> LENGTH: 1962
<212> TYPE: DNA
<213> ORGANISM: artificial sequence
<220> FEATURE:
<223> OTHER INFORMATION: Synthetic Construct; a nucleotide sequence
      coding SE36-4.

<400> SEQUENCE: 20
atgaaaaacg tgatcaaatg taccggtgaa agccagaccg gtaataccgg cggtggtcag      60
gcaggcaaca cggttggcga ccaggcgggc tctaccggcg gctctccgca gggtagcaca     120
ggcgccagtc aacccggctc tagcgaaccg tctaacccag tgtcttctgg ccattctgtt     180
agtaccgtta gcgttagcca gaccagcacc tcttctgaaa acaagatac cattcaggtg     240 aaatctgcgc tgctgaaaga ttatatgggt ttaaaagtta cgggcccgtg taacgaaaat     300
ttcatcatgt tcctggttcc gcatatttat attgatgtgg ataccgaaga taccaatata     360
gagctccgta ccacccgaa agaaaccaac aacgcgatct catttgaatc aaacagtggt     420
tcactggaaa aaaaaaata tgtgaagctt ccgtcaaacg gcaccaccgg tgaacagggt     480
tcaagtacag gcaccgttcg cggcgatacc gaaccgattt cagactcgag taccggtgaa     540
tctcaaaccg gtaacactgg tggcggtcag gcaggtaaca ccggcggaga tcaggcagga     600
agcaccggcg gcagcccgca aggaagcaca ggcgcgagtc gcagggtag cactggtgcg      660 agcccacagg gtagtacagg cgcaagtcaa cctggaagcg gatccacggg tgagtcgcaa     720
actggtaata cgggtggagg ccaagtgggc aatactggtg gtggccaggc aggttcgact     780
ggaggttctc gcaaggctc taccggtgca agccaaccag gaagcagtga accgtctaat     840
ccggtgagcg actcgagtga agtcttccg gcgaatggcc cggattcccc gaccgttaaa      900 ccccgcgta acctgcagaa catctgtgaa accggcaaaa acttcaaact ggtggtgtat     960
attaaggaga atacattaat cattaaatgg aaagtgtacg cgaaaccaa agataccacc    1020 gaaaataaca agtggacgt acgcaagtat ctgattaacg aaaaggaaac cccgtttact    1080
agtattctaa tccatgcata taccggcgaa agccaaacgg caacacagg tggtggtcag    1140 gccggtaata ctgtgggcga tcaagctggt aacaccgtgg gcgatcaggc gggctctaca    1200
ggtggcagcc ctcagggcag caccggagca tctcaacctg gtagtcttaa gacgggtgaa    1260
tcacagaccg gtaataccgg aggcggacaa gcaggtaata ccgttggagg ccaggctggt    1320
aatacgggag gtggtcaggc aggtaatact ggcggagatc cgcaaggtag taccggtgga    1380
```

```
agccaaccag gctcccatgc atataaagaa cataatggca ccaacctgat cgaaagtaaa      1440
aactacgcgc tgggctcaga cattccggaa aaatgtgata ccctggcgtc caattgcacc      1500
ggcgagagcc aaactggcaa cacgggtggt ggacaggctg gtaacactgg tggcggtcag      1560
gcaggcaata ctgttggtga tcaagctggt agtaccggcg gcagtccaca aggaagtact      1620
ggagcgagcc aaccgggctc tctcgagacg ggcgaaagtc agacgggtaa cgcaggtgga      1680
ggtcaagcag gcaacacggt tggtgaccaa gcaggtagca cgggtggaag tccgcaaggt      1740
agtacaggtg caagtccaca aggctccact ggtgcatctc acaaggttc gaccggtgca       1800 agtcagccgg gtagctccaa ttgctttctg agtggtaact ttaacattga aaatgctt       1860 cagtgcgcgc tgctggtgga aaagaaaat aaaaacgacg tgtgttacaa atacctaagc       1920
gaagatattg tgtctaattt caaggagatc aaagcggagt aa                         1962
```

<210> SEQ ID NO 21
<211> LENGTH: 1257
<212> TYPE: DNA
<213> ORGANISM: artificial sequence
<220> FEATURE:
<223> OTHER INFORMATION: Synthetic Construct; a nucleotide sequence
      coding SE36-5.

<400> SEQUENCE: 21

```
atgaaaaacg tgatcaaatg taccggtgaa agccagaccg gtaataccgg cggtggtcag       60
gcaggcaaca cggttggcga ccaggcgggc tctaccggcg gctctccgca gggtagcaca      120
ggcgccagtc aacccggctc tagcgaaccg tctaacccag tgtcttctgg ccattctgtt      180
agtaccgtta gcgttagcca gaccagcacc tcttctgaaa acaagatac cattcaggtg      240 aaatctgcgc tgctgaaaga ttatatgggt ttaaaagtta cgggcccgtg taacgaaaat      300
ttcatcatgt tcctggttcc gcatatttat attgatgtgg ataccgaaga taccaatata      360
gagctccgta ccaccctgaa agaaaccaac aacgcgatct catttgaatc aaacagtggt      420
tcactggaaa aaaaaaata tgtgaagctt ccgtcaaacg gcaccaccgg tgaacagggt      480
tcaagtacag gcaccgttcg cggcgatacc gaaccgattt cagactcgag ttctgaaccg      540
agtaacccgg ttagctctgg acatagtgtt agtaccgttt cggtttctca gacgtctacg      600
agttcggact cgagtgaaag tcttccggcg aatggcccgg attccccgac cgttaaaccc      660
ccgcgtaacc tgcagaacat ctgtgaaacc ggcaaaaact tcaaactggt ggtgtatatt      720
aaggagaata cattaatcat taaatggaaa gtgtacggcg aaaccaaaga taccaccgaa      780
aataacaaag tggacgtacg caagtatctg attaacgaaa aggaaacccc gtttactagt      840
attctaatcc atgcatatag cgagccgtct aatccagtga gctctggtca ttccgttagc      900
accgtgagcg tgagtcagac gagcacgagc tcgcatgcat ataaagaaca taatggcacc      960
aacctgatcg aaagtaaaaa ctacgcgctg gctcagaca ttccggaaaa atgtgatacc      1020
ctggcgtcca attgcagcga accgagcaac ccggtgagca gtggacatag cgtgagcacc      1080
gttagcgtta gtcagaccctc gaccagcagt tccaattgct ttctgagtgg taactttaac      1140
attgaaaaat gctttcagtg cgcgctgctg gtggaaaag aaaataaaaa cgacgtgtgt      1200
tacaaatacc taagcgaaga tattgtgtct aatttcaagg agatcaaagc ggagtaa        1257
```

<210> SEQ ID NO 22
<211> LENGTH: 795
<212> TYPE: DNA
<213> ORGANISM: artificial sequence
<220> FEATURE:
<223> OTHER INFORMATION: Synthetic Construct; a nucleotide sequence coding negative SE36.

<400> SEQUENCE: 22

```
atgtctgaaa aacaagatac cattcaggtg aaatctgcgc tgctgaaaga ttatatgggt      60
ttaaaagtta cgggcccgtg taacgaaaat ttcatcatgt tcctggttcc gcatatttat     120
attgatgtgg ataccgaaga taccaatata gagctccgta ccaccctgaa agaaaccaac     180
aacgcgatct catttgaatc aaacagtggt tcactggaaa aaaaaaaata tgtgaagctt     240
ccgtcaaacg gcaccaccgg tgaacagggt tcaagtacag gcaccgttcg cggcgatacc     300
gaaccgattt cagactcgag tgaaagtctt ccggcgaatg gcccggattc cccgaccgtt     360
aaaccccgc gtaacctgca gaacatctgt gaaaccggca aaaacttcaa actggtggtg     420
tatattaagg agaatacatt aatcattaaa tggaaagtgt acggcgaaac caaagatacc     480
accgaaaata acaaagtgga cgtacgcaag tatctgatta cgaaaagga accccgttt      540
actagtattc taatccatgc atataaagaa cataatggcc caacctgat cgaaagtaaa     600
aactacgcgc tgggctcaga cattccggaa aaatgtgata ccctggcgtc caattgcttt     660
ctgagtggta actttaacat tgaaaaatgc tttcagtgcg cgctgctggt ggaaaaagaa     720
aataaaaacg acgtgtgtta caaataccta agcgaagata ttgtgtctaa tttcaaggag     780
atcaaagcgg agtaa                                                     795
```

<210> SEQ ID NO 23
<211> LENGTH: 42
<212> TYPE: PRT
<213> ORGANISM: artificial sequence
<220> FEATURE:
<223> OTHER INFORMATION: Synthetic Construct; an amino acid sequence of polypetide for epitope mapping.

<400> SEQUENCE: 23

```
Met Lys Asn Val Ile Lys Cys Thr Gly Glu Ser Gln Thr Gly Asn Thr
  1               5                  10                  15
Gly Gly Gly Gln Ala Gly Asn Thr Val Gly Asp Gln Ala Gly Ser Thr
             20                  25                  30
Gly Gly Ser Pro Gln Gly Ser Thr Gly Ala
         35                  40
```

<210> SEQ ID NO 24
<211> LENGTH: 42
<212> TYPE: PRT
<213> ORGANISM: artificial sequence
<220> FEATURE:
<223> OTHER INFORMATION: Synthetic Construct; an amino acid sequence of polypeptide for epitope mapping.

<400> SEQUENCE: 24

```
Asn Thr Val Gly Asp Gln Ala Gly Ser Thr Gly Gly Ser Pro Gln Gly
  1               5                  10                  15
Ser Thr Gly Ala Ser Gln Pro Gly Ser Ser Glu Pro Ser Asn Pro Val
             20                  25                  30
Ser Ser Gly His Ser Val Ser Thr Val Ser
         35                  40
```

<210> SEQ ID NO 25
<211> LENGTH: 42
<212> TYPE: PRT
<213> ORGANISM: artificial sequence

```
<220> FEATURE:
<223> OTHER INFORMATION: Synthetic Construct; an amino acid sequence of
      polypeptide for epitope mapping.

<400> SEQUENCE: 25

Ser Gln Pro Gly Ser Ser Glu Pro Ser Asn Pro Val Ser Ser Gly His
1               5                   10                  15

Ser Val Ser Thr Val Ser Val Ser Gln Thr Ser Thr Ser Ser Glu Lys
            20                  25                  30

Gln Asp Thr Ile Gln Val Lys Ser Ala Leu
        35                  40

<210> SEQ ID NO 26
<211> LENGTH: 42
<212> TYPE: PRT
<213> ORGANISM: artificial sequence
<220> FEATURE:
<223> OTHER INFORMATION: Synthetic Construct; an amino acid sequence of
      polypeptide for epitope mapping.

<400> SEQUENCE: 26

Val Ser Gln Thr Ser Thr Ser Ser Glu Lys Gln Asp Thr Ile Gln Val
1               5                   10                  15

Lys Ser Ala Leu Leu Lys Asp Tyr Met Gly Leu Lys Val Thr Gly Pro
            20                  25                  30

Cys Asn Glu Asn Phe Ile Met Phe Leu Val
        35                  40

<210> SEQ ID NO 27
<211> LENGTH: 42
<212> TYPE: PRT
<213> ORGANISM: artificial sequence
<220> FEATURE:
<223> OTHER INFORMATION: Synthetic Construct; an amino acid sequence of
      polypeptide for epitope mapping.

<400> SEQUENCE: 27

Leu Lys Asp Tyr Met Gly Leu Lys Val Thr Gly Pro Cys Asn Glu Asn
1               5                   10                  15

Phe Ile Met Phe Leu Val Pro His Ile Tyr Ile Asp Val Asp Thr Glu
            20                  25                  30

Asp Thr Asn Ile Glu Leu Arg Thr Thr Leu
        35                  40

<210> SEQ ID NO 28
<211> LENGTH: 42
<212> TYPE: PRT
<213> ORGANISM: artificial sequence
<220> FEATURE:
<223> OTHER INFORMATION: Synthetic Construct; an amino acid sequence of
      polypeptide for epitope mapping.

<400> SEQUENCE: 28

Pro His Ile Tyr Ile Asp Val Asp Thr Glu Asp Thr Asn Ile Glu Leu
1               5                   10                  15

Arg Thr Thr Leu Lys Glu Thr Asn Asn Ala Ile Ser Phe Glu Ser Asn
            20                  25                  30

Ser Gly Ser Leu Glu Lys Lys Lys Tyr Val
        35                  40

<210> SEQ ID NO 29
<211> LENGTH: 42
<212> TYPE: PRT
```

```
<213> ORGANISM: artificial sequence
<220> FEATURE:
<223> OTHER INFORMATION: Synthetic Construct; an amino acid sequence of
      polypeptide for epitope mapping.

<400> SEQUENCE: 29

Lys Glu Thr Asn Asn Ala Ile Ser Phe Glu Ser Asn Ser Gly Ser Leu
1               5                   10                  15

Glu Lys Lys Lys Tyr Val Lys Leu Pro Ser Asn Gly Thr Thr Gly Glu
            20                  25                  30

Gln Gly Ser Ser Thr Gly Thr Val Arg Gly
        35                  40

<210> SEQ ID NO 30
<211> LENGTH: 42
<212> TYPE: PRT
<213> ORGANISM: artificial sequence
<220> FEATURE:
<223> OTHER INFORMATION: Synthetic Construct; an amino acid sequence of
      polypeptide for epitope mapping.

<400> SEQUENCE: 30

Lys Leu Pro Ser Asn Gly Thr Thr Gly Glu Gln Gly Ser Ser Thr Gly
1               5                   10                  15

Thr Val Arg Gly Asp Thr Glu Pro Ile Ser Asp Ser Ser Glu Ser Leu
            20                  25                  30

Pro Ala Asn Gly Pro Asp Ser Pro Thr Val
        35                  40

<210> SEQ ID NO 31
<211> LENGTH: 42
<212> TYPE: PRT
<213> ORGANISM: artificial sequence
<220> FEATURE:
<223> OTHER INFORMATION: Synthetic Construct; an amino acid sequence of
      polypeptide for epitope mapping.

<400> SEQUENCE: 31

Asp Thr Glu Pro Ile Ser Asp Ser Ser Glu Ser Leu Pro Ala Asn Gly
1               5                   10                  15

Pro Asp Ser Pro Thr Val Lys Pro Pro Arg Asn Leu Gln Asn Ile Cys
            20                  25                  30

Glu Thr Gly Lys Asn Phe Lys Leu Val Val
        35                  40

<210> SEQ ID NO 32
<211> LENGTH: 42
<212> TYPE: PRT
<213> ORGANISM: artificial sequence
<220> FEATURE:
<223> OTHER INFORMATION: Synthetic Construct; an amino acid sequence of
      polypeptide for epitope mapping.

<400> SEQUENCE: 32

Lys Pro Pro Arg Asn Leu Gln Asn Ile Cys Glu Thr Gly Lys Asn Phe
1               5                   10                  15

Lys Leu Val Val Tyr Ile Lys Glu Asn Thr Leu Ile Ile Lys Trp Lys
            20                  25                  30

Val Tyr Gly Glu Thr Lys Asp Thr Thr Glu
        35                  40

<210> SEQ ID NO 33
<211> LENGTH: 42
```

```
<212> TYPE: PRT
<213> ORGANISM: artificial sequence
<220> FEATURE:
<223> OTHER INFORMATION: Synthetic Construct; an amino acid sequence of
      polypeptide for epitope mapping.

<400> SEQUENCE: 33

Tyr Ile Lys Glu Asn Thr Leu Ile Ile Lys Trp Lys Val Tyr Gly Glu
1               5                   10                  15

Thr Lys Asp Thr Thr Glu Asn Asn Lys Val Asp Val Arg Lys Tyr Leu
            20                  25                  30

Ile Asn Glu Lys Glu Thr Pro Phe Thr Ser
        35                  40

<210> SEQ ID NO 34
<211> LENGTH: 42
<212> TYPE: PRT
<213> ORGANISM: artificial sequence
<220> FEATURE:
<223> OTHER INFORMATION: Synthetic Construct; an amino acid sequence of
      polypeptide for epitope mapping.

<400> SEQUENCE: 34

Asn Asn Lys Val Asp Val Arg Lys Tyr Leu Ile Asn Glu Lys Glu Thr
1               5                   10                  15

Pro Phe Thr Ser Ile Leu Ile His Ala Tyr Lys Glu His Asn Gly Thr
            20                  25                  30

Asn Leu Ile Glu Ser Lys Asn Tyr Ala Leu
        35                  40

<210> SEQ ID NO 35
<211> LENGTH: 42
<212> TYPE: PRT
<213> ORGANISM: artificial sequence
<220> FEATURE:
<223> OTHER INFORMATION: Synthetic Construct; an amino acid sequence of
      polypeptide for epitope mapping.

<400> SEQUENCE: 35

Ile Leu Ile His Ala Tyr Lys Glu His Asn Gly Thr Asn Leu Ile Glu
1               5                   10                  15

Ser Lys Asn Tyr Ala Leu Gly Ser Asp Ile Pro Glu Lys Cys Asp Thr
            20                  25                  30

Leu Ala Ser Asn Cys Phe Leu Ser Gly Asn
        35                  40

<210> SEQ ID NO 36
<211> LENGTH: 42
<212> TYPE: PRT
<213> ORGANISM: artificial sequence
<220> FEATURE:
<223> OTHER INFORMATION: Synthetic Construct; an amino acid sequence of
      polypeptide for epitope mapping.

<400> SEQUENCE: 36

Gly Ser Asp Ile Pro Glu Lys Cys Asp Thr Leu Ala Ser Asn Cys Phe
1               5                   10                  15

Leu Ser Gly Asn Phe Asn Ile Glu Lys Cys Phe Gln Cys Ala Leu Leu
            20                  25                  30

Val Glu Lys Glu Asn Lys Asn Asp Val Cys
        35                  40

<210> SEQ ID NO 37
```

```
<211> LENGTH: 40
<212> TYPE: PRT
<213> ORGANISM: artificial sequence
<220> FEATURE:
<223> OTHER INFORMATION: Synthetic Construct; an amino acid sequence of
      polypeptide for epitope mapping.

<400> SEQUENCE: 37

Phe Asn Ile Glu Lys Cys Phe Gln Cys Ala Leu Leu Val Glu Lys Glu
1               5                   10                  15

Asn Lys Asn Asp Val Cys Tyr Lys Tyr Leu Ser Glu Asp Ile Val Ser
            20                  25                  30

Asn Phe Lys Glu Ile Lys Ala Glu
            35                  40
```